United States Patent
Yaver et al.

(10) Patent No.: US 6,942,973 B2
(45) Date of Patent: Sep. 13, 2005

(54) METHODS FOR ISOLATING GENES FROM MICROORGANISMS

(75) Inventors: Debbie S. Yaver, Davis, CA (US); Randy M. Berka, Davis, CA (US)

(73) Assignee: Novozymes Biotech, Inc., Davis, CA (US)

( * ) Notice: Subject to any disclaimer, the term of this patent is extended or adjusted under 35 U.S.C. 154(b) by 0 days.

(21) Appl. No.: 10/095,975

(22) Filed: Mar. 12, 2002

(65) Prior Publication Data

US 2003/0013182 A1 Jan. 16, 2003

Related U.S. Application Data

(60) Provisional application No. 60/275,283, filed on Mar. 12, 2001.

(51) Int. Cl.[7] ........................... C12Q 1/68; C12P 21/02; C12N 9/08; C07H 21/04
(52) U.S. Cl. ........................ 435/6; 435/69.1; 435/192; 536/23.2; 536/23.7
(58) Field of Search .......................... 435/6, 69.1, 192; 536/23.2, 23.7

(56) References Cited

U.S. PATENT DOCUMENTS

2002/0146721 A1 * 10/2002 Berka et al. ................... 435/6

OTHER PUBLICATIONS

Whitman et al., Expression of fungal MN peroxidase in *E. Coli* and refolding to yield active enzyme, 1995, Biochemical and Biophtsical Research Communications, vol. 216, pp. 1013–1017.*

Mayfield et al., Characterization of the mnp2 gene encoding manganese peroxidase isozyme 2 from the basidiomycete *phanerochaete chrysosporium*, 1994, GENE, vol. 142, pp. 213–235.*

Schena, Genome analysis with gene expression microassays, 1996, BIOESSAYS, vol. 18, pp. 427–431.*

Brzostowica et al., Simultaneous identification of two cyclohexanone oxidation genes from an environmental *brevibacterium* isolate using mRNA differential display, 2000, Journal of Bacteriology, vol. 182, pp. 4241–4248.*

Watson et al., Gene chips and array revealed: A primer on their power and their uses, 1999, Biological Psychiatry, vol. 45, pp. 533–543.*

DeRisi et al., Exploring the metabolic and genetic control of gene expression on a genomic scale, 1997, SCIENCE, vol. 278, pp. 680–686.*

* cited by examiner

*Primary Examiner*—David Guzo
*Assistant Examiner*—Daniel M. Sullivan
(74) *Attorney, Agent, or Firm*—Robert L. Starnes, Esq.

(57) ABSTRACT

The present invention relates to methods for isolating a gene encoding an enzyme, comprising: (a) adding a mixture of labeled first nucleic acid probes from a microbial strain cultured on medium without the substrate, and labeled second nucleic acid probes from a microbial strain cultured on medium with the substrate, to an array of random nucleic acid fragments of the microbial strain where the labeled nucleic acids hybridize to complementary sequences of the genomic fragments in the array, wherein the first nucleic acid probes are labeled with a first reporter and the second nucleic acid probes are labeled with a second reporter; (b) examining the array under conditions wherein the relative expression of the genes of the microbial strain is determined by the observed hybridization reporter signal of each spot in the array; and (c) isolating a gene from the microbial strain that encodes an enzyme that degrades the substrate. The present invention also relates to isolated genes obtained by such methods.

57 Claims, 1 Drawing Sheet

```
      M   A   F   A   S   L   F   T   L   V   V   L   A   A   V   S   N   A   A   P
   1  ATGGCTTTCGCCTCTCTCTTTACCCTCGTTGTGCTCGCCGCAGTCTCAAACGCTGCACCG
      T   A   V   C   A   D   G   T   R   V   S   N   A   A   C   A   F   I   P
  61  ACTGCTGTCTGCGCTGACGGCACTCGCGTCAGCAATGCAGCCTGCTGCGCCTTCATCCCA
      L   A   Q   D   L   Q   E   T   L   F   M   G   D   C   G   E   D   A   H   E
 121  CTCGCACAGGATCTGCAAGAGACGCTCTTCATGGGCGACTGCGGTGAAGATGCTCACGAG
      V   I   R   L   T   F   H   D   A   V   A   I   S   S   S   M   G   P   S   A
 181  GTCATCCGGTTGACCTTCCACGACGCTGTTGCGATCTCCAGCAGCATGGGCCCCTCTGCC
      G   G   A   D   G   S   M   L   L   F   P   T   V   E   P   N   F   S   A
 241  GGCGGTGGAGCTGACGGTTCGATGCTTTTGTTCCCCACGGTCGAGCCAAATTTCTCGGCC
      N   N   G   I   D   D   S   V   N   N   L   I   P   F   L   S   K   H   A   V
 301  AACAACGGTATCGACGACTCCGTGAACAACCTCATTCCCTTCCTGTCGAAGCACGCCGTT
      S   A   G   D   L   V   Q   F   A   G   A   V   A   L   T   N   C   P   G   A
 361  AGCGCGGGTGATCTCGTTCAGTTTGCGGGTGCTGTCGCTTTGACCAACTGTCCTGGCGCT
      P   R   L   E   F   L   A   G   R   P   N   H   T   I   A   A   I   D   G   L
 421  CCTCGGCTCGAATTCTTGGCTGGTCGCCCTAACCACACCATCGCTGCCATCGATGGCCTG
      I   P   E   P   Q   D   D   V   T   K   I   L   A   R   F   E   D   A   G   G
 481  ATCCCTGAGCCTCAGGACGATGTCACCAAGATTCTCGCACGCTTCGAAGATGCCGGAGGC
      F   S   P   F   E   V   V   S   L   L   A   S   H   T   V   A   R   A   D   K
 541  TTCAGCCCCTTCGAAGTTGTCTCACTCCTGGCTTCCCACACCGTCGCCCGCGCTGACAAG
      V   D   G   T   I   D   A   A   P   F   D   S
 601  GTCGATGGGACCATTGATGCGGCACCTTTCGACTCGGTCAGTGCTCGTCTGGAACTCAAG
                                                      T   P   F   T   F   D   T   Q   V
 661  CTTCATGCTTTATATTGACATCGTGGTACACTAGACCCCGTTCACCTTCGACACTCAGGT
       F   L   E   V   L   L   K   G   T   G   F   P   G   T   N   N   N   T   G   E
 721  ATTCCTTGAGGTGCTGCTCAAGGGTACTGGTTTCCCTGGAACCAACAACAACACTGGCGA
       V   A   S   P   L   P   L   T   S   G   N   D   T   G   E   M   R   L   Q   S
 781  GGTTGCGTCTCCTCTCCCACTCACCAGTGGCAACGACACTGGTGAAATGCGCCTCCAGTC
       D   F   A   L   A   R   D   E   R   T   A   C   F   W   Q   S   F   V   N   E
 841  CGACTTTGCTCTTGCCCGCGACGAACGCACCGCTTGCTTCTGGCAGAGCTTCGTCAACGA
       Q   E   F   M   A   Q   S   F   K   A   A   M   S   K   L   A   V   L   G   H
 901  GCAGGAGTTCATGGCACAAAGCTTCAAGGCCGCGATGTCCAAGCTCGCAGTCCTCGGCCA
       S   R   S   S   L   V   D   C   S   D   V   V   P   A   P   K   P   A   V   N
 961  CAGCCGCTCGAGCCTAGTCGACTGCTCAGACGTCGTCCCCGCGCCGAAGCCCGCCGTGAA
       K   P   A   T   F   P   A   T   T   G   P   D   D   L   E   L   T   C   T   A
1021  CAAGCCCGCGACGTTCCCCGCCACCACTGGTCCAGATGACCTCGAGCTCACCTGCACGGC
       E   R   F   P   T   L   S   V   D
1081  AGAGCGCTTCCCGACACTCTCCGTTGACCGTGAGTGTCTCAGCCTCAGTGATACAGATGC
                                                       P   G   A   Q   Q   T   L   I   P   H   C   S
1141  ATGATTGACCTTGATGTCTTCGATAGCTGGTGCGCAGCAGACGCTCATTCCGCACTGCTC
       D   G   D   Q   V   C   A   T   V   Q   F   T   G   P   A
1201  CGACGGTGACCAGGTATGCGCGACCGTCCAATTTACTGGCCCTGCTTAG
```

Fig. 1

SEQUENCE LISTING

<160> NUMBER OF SEQ ID NOS: 10

<210> SEQ ID NO 1
<211> LENGTH: 1249
<212> TYPE: DNA
<213> ORGANISM: Ceriporiopsis subvermispora

<400> SEQUENCE: 1

```
atggctttcg cctctctctt taccctcgtt gtgctcgccg cagtctcaaa cgctgcaccg      60
actgctgtct gcgctgacgg cactcgcgtc agcaatgcag cctgctgcgc cttcatccca     120
ctcgcacagg atctgcaaga gacgctcttc atgggcgact gcggtgaaga tgctcacgag     180
gtcatccggt tgaccttcca cgacgctgtt gcgatctcca gcagcatggg cccctctgcc     240
ggcggtggag ctgacggttc gatgcttttg ttccccacgg tcgagccaaa tttctcggcc     300
aacaacggta tcgacgactc cgtgaacaac ctcattccct tcctgtcgaa gcacgccgtt     360
agcgcgggtg atctcgttca gtttgcgggt gctgtcgctt tgaccaactg tcctggcgct     420
cctcggctcg aattcttggc tggtcgccct aaccacacca tcgctgccat cgatggcctg     480
atccctgagc ctcaggacga tgtcaccaag attctcgcac gcttcgaaga tgccggaggc     540 ttcagccccct tcgaagttgt ctcactcctg gcttcccaca ccgtcgcccg cgctgacaag     600
gtcgatggga ccattgatgc ggcaccttc gactcggtca gtgctcgtct ggaactcaag     660
cttcatgctt tatattgaca tcgtggtaca ctagacccg ttcaccttcg acactcaggt     720
attccttgag gtgctgctca agggtactgg tttccctgga accaacaaca acactggcga     780
ggttgcgtct cctctcccac tcaccagtgg caacgacact ggtgaaatgc gcctccagtc     840
cgactttgct cttgcccgcg acgaacgcac cgcttgcttc tggcagagct tcgtcaacga     900
gcaggagttc atggcacaaa gcttcaaggc cgcgatgtcc aagctcgcag tcctcggcca     960
cagccgctcg agcctagtcg actgctcaga cgtcgtcccc gcgccgaagc ccgccgtgaa    1020
caagcccgcg acgttccccg ccaccactgg tccagatgac ctcgagctca cctgcacggc    1080
agagcgcttc ccgacactct ccgttgaccg tgagtgtctc agcctcagtg atacagatgc    1140
atgattgacc ttgatgtctt cgatagctgg tgcgcagcag acgctcattc cgcactgctc    1200
```

-continued cgacggtgac caggtatgcg cgaccgtcca atttactggc cctgcttag            1249

<210> SEQ ID NO 2
<211> LENGTH: 376
<212> TYPE: PRT
<213> ORGANISM: Ceriporiopsis subvermispora

<400> SEQUENCE: 2

```
Met Ala Phe Ala Ser Leu Phe Thr Leu Val Leu Ala Ala Val Ser
 1               5                  10                  15

Asn Ala Ala Pro Thr Ala Val Cys Ala Asp Gly Thr Arg Val Ser Asn
                20                  25                  30

Ala Ala Cys Cys Ala Phe Ile Pro Leu Ala Gln Asp Leu Gln Glu Thr
             35                  40                  45

Leu Phe Met Gly Asp Cys Gly Glu Asp Ala His Glu Val Ile Arg Leu
         50                  55                  60

Thr Phe His Asp Ala Val Ala Ile Ser Ser Met Gly Pro Ser Ala
 65                  70                  75                  80

Gly Gly Gly Ala Asp Gly Ser Met Leu Leu Phe Pro Thr Val Glu Pro
                 85                  90                  95

Asn Phe Ser Ala Asn Asn Gly Ile Asp Asp Ser Val Asn Asn Leu Ile
                100                 105                 110

Pro Phe Leu Ser Lys His Ala Val Ser Ala Gly Asp Leu Val Gln Phe
            115                 120                 125

Ala Gly Ala Val Ala Leu Thr Asn Cys Pro Gly Ala Pro Arg Leu Glu
        130                 135                 140

Phe Leu Ala Gly Arg Pro Asn His Thr Ile Ala Ala Ile Asp Gly Leu
145                 150                 155                 160

Ile Pro Glu Pro Gln Asp Asp Val Thr Lys Ile Leu Ala Arg Phe Glu
                165                 170                 175

Asp Ala Gly Gly Phe Ser Pro Phe Glu Val Val Ser Leu Leu Ala Ser
            180                 185                 190

His Thr Val Ala Arg Ala Asp Lys Val Asp Gly Thr Ile Asp Ala Ala
        195                 200                 205

Pro Asp Ser Thr Pro Phe Thr Phe Asp Thr Gln Val Phe Leu Glu Val
    210                 215                 220

Leu Leu Lys Gly Thr Gly Phe Pro Gly Thr Asn Asn Thr Gly Glu
225                 230                 235                 240

Val Ala Ser Pro Leu Pro Leu Thr Ser Gly Asn Asp Thr Gly Glu Met
                245                 250                 255

Arg Leu Gln Ser Asp Phe Ala Leu Ala Arg Asp Glu Arg Thr Ala Cys
            260                 265                 270

Phe Trp Gln Ser Phe Val Asn Glu Gln Glu Phe Met Ala Gln Ser Phe
        275                 280                 285

Lys Ala Ala Met Ser Lys Leu Ala Val Leu Gly His Ser Arg Ser Ser
    290                 295                 300

Leu Val Asp Cys Ser Asp Val Val Pro Ala Pro Lys Pro Ala Val Asn
305                 310                 315                 320

Lys Pro Ala Thr Phe Pro Ala Thr Thr Gly Pro Asp Leu Glu Leu
                325                 330                 335

Thr Cys Thr Ala Glu Arg Phe Pro Thr Leu Ser Val Asp Pro Gly Ala
            340                 345                 350

Gln Gln Thr Leu Ile Pro His Cys Ser Asp Gly Asp Gln Val Cys Ala
        355                 360                 365
```

Thr Val Gln Phe Thr Gly Pro Ala
    370             375

<210> SEQ ID NO 3
<211> LENGTH: 44
<212> TYPE: DNA
<213> ORGANISM: Artificial Sequence
<220> FEATURE:
<223> OTHER INFORMATION: Ceriporiopsis subvermispora

<400> SEQUENCE: 3
cgacuggagc acgaggacac ugacauggac ugaaggagua gaaa                44

<210> SEQ ID NO 4
<211> LENGTH: 26
<212> TYPE: DNA
<213> ORGANISM: Artificial Sequence
<220> FEATURE:
<223> OTHER INFORMATION: Ceriporiopsis subvermispora

<400> SEQUENCE: 4
tcgaaaggtg ccgcatcaat ggtccc                                    26

<210> SEQ ID NO 5
<211> LENGTH: 26
<212> TYPE: DNA
<213> ORGANISM: Artificial Sequence
<220> FEATURE:
<223> OTHER INFORMATION: Ceriporiopsis subvermispora

<400> SEQUENCE: 5
ttcgtcgcgg gcaagagcaa agtcgg                                    26

<210> SEQ ID NO 6
<211> LENGTH: 26
<212> TYPE: DNA
<213> ORGANISM: Artificial Sequence
<220> FEATURE:
<223> OTHER INFORMATION: Ceriporiopsis subvermispora

<400> SEQUENCE: 6
acggtcaacg gagagtgtcg ggaagc                                    26

<210> SEQ ID NO 7
<211> LENGTH: 23
<212> TYPE: DNA
<213> ORGANISM: Artificial Sequence
<220> FEATURE:
<223> OTHER INFORMATION: Ceriporiopsis subvermispora

<400> SEQUENCE: 7
cgactggagc acgaggacac tga                                       23

<210> SEQ ID NO 8
<211> LENGTH: 24
<212> TYPE: DNA
<213> ORGANISM: Artificial Sequence
<220> FEATURE:
<223> OTHER INFORMATION: Ceriporiopsis subvermispora

<400> SEQUENCE: 8
ccccatggct ttcgcctctc tctt                                      24

<210> SEQ ID NO 9
<211> LENGTH: 23

```
-continued

<212> TYPE: DNA
<213> ORGANISM: Artificial Sequence
<220> FEATURE:
<223> OTHER INFORMATION: Ceriporiopsis subvermispora

<400> SEQUENCE: 9
gaattcttgg ctggtcgccc taa                                           23

<210> SEQ ID NO 10
<211> LENGTH: 29
<212> TYPE: DNA
<213> ORGANISM: Artificial Sequence
<220> FEATURE:
<223> OTHER INFORMATION: Ceriporiopsis subvermispora

<400> SEQUENCE: 10
aagttaatta actaagcagg gccagtaaa                                     29
```

METHODS FOR ISOLATING GENES FROM MICROORGANISMS

CROSS-REFERENCE TO RELATED APPLICATION

This application claims priority from pending U.S. provisional application Ser. No. 60/275,283 filed on Mar. 12, 2001, which application is fully incorporated herein by reference.

BACKGROUND OF THE INVENTION

1. Field of the Invention

The present invention relates to methods for isolating a gene encoding an enzyme from a microorganism and to genes isolated by such methods.

2. Description of the Related Art

Traditionally the isolation of a gene from a microorganism begins with the isolation and partial amino acid sequencing of a protein. Degenerate oligonucleotides are then synthesized from the partial amino acid sequences and used to isolate the gene from the microorganism. A typical method used to isolate the gene is PCR employing the degenerate oligonucleotides.

Lignin is an aromatic polymer occurring in the woody tissue of higher plants. Due to its hydrophobicity and complex random structure lacking regular hydrolyzable bonds, lignin is poorly degraded by most organisms. The best degraders of lignin are white rot fungi that produce extracellular peroxidases and laccases, which are involved in the initial attack of lignin.

Manganese-dependent peroxidase is a frequently encountered peroxidase produced by white rot fungi. The peroxidase has a catalytic cycle involving a 2-electron oxidation of the heme by hydrogen peroxide and subsequent oxidation of compound I via compound II in two 1-electron steps to the native enzyme. The best reducing substrate for compounds I and II is Mn(II), a metal naturally present in wood. The Mn(III) formed oxidizes other substrates. Organic acids such as oxalate, glyoxylate and lactate are known to have an important role in the mechanism of manganese-dependent peroxidase and lignin degradation. Mn(III) is stripped from the enzyme by organic acids, and the produced Mn(III)-organic acid complex acts as a diffusible mediator in the oxidation of lignin by manganese-dependent peroxidase. Mn(III) can also oxidize organic acids, yielding radicals. The organic acids may also be supplied from the degradation of lignin and by microorganisms.

There is a need in the art for new methods that enable the identification and isolation of a number of genes from a microorganism that encode enzymes that degrade a particular substrate.

The object of the present invention is to provide methods for isolating genes from microorganisms.

SUMMARY OF THE INVENTION

The present invention relates to methods for isolating a gene encoding an enzyme, comprising: (a) adding a mixture of labeled first nucleic acid probes, isolated from a microbial strain cultured on medium without the substrate, and labeled second nucleic acid probes, isolated from the microbial strain cultured on medium with the substrate, to an array of random nucleic acid fragments of the microbial strain under conditions where the labeled nucleic acids hybridize to complementary sequences of the genomic fragments in the array, wherein the first nucleic acid probes are labeled with a first reporter and the second nucleic acid probes are labeled with a second reporter;

(b) examining the array under conditions wherein the relative expression of the genes of the microbial strain is determined by the observed hybridization reporter signal of each spot in the array in which (i) the genomic fragments in the array that hybridize to the first nucleic acid probes produce a distinct first hybridization reporter signal or the second nucleic acid probes produce a distinct second hybridization reporter signal, and (ii) the genomic fragments in the array that hybridize to both the first and second nucleic acid probes produce a distinct combined hybridization reporter signal; and (c) isolating a gene from the microbial strain that encodes an enzyme that degrades the substrate.

The present invention also relates to genes isolated by such methods and nucleic acid constructs, vectors, and host cells containing the genes.

The present invention further relates to isolated polypeptides having peroxidase activity selected from the group consisting of:

(a) a polypeptide having an amino acid sequence which has at least 85% identity with amino acids 19 to 316 of SEQ ID NO:2;

(b) a polypeptide encoded by a nucleic acid sequence which hybridizes under medium-high stringency conditions with (i) nucleotides 55 to 1249 of SEQ ID NO:1, (ii) the genomic sequence comprising or cDNA sequence contained in nucleotides 55 to 1249 of SEQ ID NO:1, or (iii) a complementary strand of (i) or (ii);

(c) an allelic variant of (a) or (b); and (e) a fragment of (a), (b), or (c) that has peroxidase activity.

The present invention also relates to isolated nucleic acid sequences encoding the polypeptides and to nucleic acid constructs, vectors, and host cells comprising the nucleic acid sequences as well as methods for producing and using the polypeptides.

BRIEF DESCRIPTION OF THE FIGURES

FIG. 1 shows the DNA sequence and the deduced amino acid sequence of a *Ceriporiopsis subvermispora* FPL 104807SS-5 (Forest Products Laboratory, Madison, Wis.) peroxidase (SEQ ID NOs:1 and 2, respectively).

DETAILED DESCRIPTION OF THE INVENTION

The present invention relates to methods for isolating a gene encoding an enzyme from a microbial strain. The method first comprises the addition of a mixture of first labeled nucleic acid probes, isolated from a microbial strain cultured on medium without the substrate, and a mixture of second labeled nucleic acid probes, isolated from the microbial strain cultured on medium with the substrate, to an array of random nucleic acid fragments of the microbial strain under conditions where the labeled nucleic acid probes hybridize to complementary sequences of the nucleic acid fragments in the array. The first nucleic acid probes are labeled with a first reporter and the second nucleic acid probes are labeled with a second reporter. The array is then examined under conditions wherein the relative expression of the genes of the microbial strain is determined by the observed hybridization reporter signal of each spot in the array in which (i) the nucleic acid fragments in the array that hybridize to the first nucleic acid probes produce a distinct first hybridization reporter signal or to the second nucleic acid probes produce a distinct second hybridization reporter signal, and (ii) the nucleic acid fragments in the array that hybridize to both the first and second nucleic acid probes produce a distinct combined hybridization reporter signal. The nucleic acid fragment is then sequenced to isolate from the microbial strain the corresponding gene that encodes an enzyme that degrades the substrate.

Enzyme

The gene of interest may encode any enzyme including an oxidoreductase, transferase, hydrolase, lyase, isomerase, or ligase. In a preferred embodiment, the enzyme is an alpha-glucosidase, aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, glucocerebrosidase, alpha-glucosidase, beta-glucosidase, hemicellulase, invertase, laccase, lignase, lipase, mannosidase, mutanase, oxidase, pectinolytic enzyme, peroxidase, phospholipase, phytase, polyphenoloxidase, proteolytic enzyme, ribonuclease, transglutaminase, urokinase, or xylanase.

In a preferred embodiment, the gene of interest encodes an enzyme which degrades lignin. In a more preferred embodiment, the gene of interest encodes a peroxidase. In a most preferred embodiment, the gene of interest encodes a manganese-dependent peroxidase.

Substrate

The substrate may be any substrate that is subject to the action of an enzyme. In a preferred embodiment, the substrate is lignin or a lignin-containing material. In another preferred embodiment, the substrate is cellulose. In another preferred embodiment, the substrate is hemicellulose. In another preferred embodiment, the substrate is pectin. In another preferred embodiment, the substrate is a lipid. In another preferred embodiment, the substrate is phospholipid. In another preferred embodiment, the substrate is phytic acid. In another preferred embodiment, the substrate is protein. In another preferred embodiment, the substrate is a starch.

In a more preferred embodiment, the protein substrate is blood, casein, egg, gelatin, gluten, milk protein, or soy protein. In another preferred embodiment, the lignin-containing material is hardwood thermomechanical pulp.

Microbial Strains

In the methods of the present invention, the microbial strain may be any microbial strain. The strain is cultured on a suitable nutrient medium with and without a substrate of interest. The strain cultured on medium without the substrate is used as a reference for identifying differences in expression of the same or similar complement of genes in the strain cultured on medium with substrate. The strain may be a wild-type, mutant, or recombinant strain.

In the methods of the present invention, the microbial strain may be a unicellular microorganism, e.g., a prokaryote, or a non-unicellular microorganism, e.g., a eukaryote. The eukaryote may be fungal strain or a mammalian or insect cell. The cell may also be a plant cell.

In a preferred embodiment, the unicellular microorganism is a bacterium. In a more preferred embodiment, the bacterium is a *Bacillus, Pseudomonas,* or *Streptomyces* strain or *E. coli.*

The *Bacillus* strain may be any *Bacillus* strain. In a preferred embodiment, the *Bacillus* strain is *Bacillus alkalophilus, Bacillus amyloliquefaciens, Bacillus brevis, Bacillus circulans, Bacillus clausii, Bacillus firmus, Bacillus lentus, Bacillus licheniformis, Bacillus megaterium, Bacillus pumilus, Bacillus stearothermophilus, Bacillus subtilis,* or *Bacillus thuringiensis.*

The *Streptomyces* strain may be any *Streptomyces* strain. In a preferred embodiment, the *Streptomyces* strain is *Streptomyces lividans.* In another preferred embodiment, the *Streptomyces* strain is *Streptomyces murinus.*

In a preferred embodiment, the strain is a fungal strain. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal strain is a yeast strain. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

In an even more preferred embodiment, the yeast strain is a *Candida, Hansenula, Kluyveromyces, Pichia, Saccharomyces, Schizosaccharomyces,* or *Yarrowia* strain.

In a most preferred embodiment, the yeast strain is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* strain. In another most preferred embodiment, the yeast strain is a *Kluyveromyces lactis* strain. In another most preferred embodiment, the yeast strain is a *Yarrowia lipolytica* strain.

In another more preferred embodiment, the fungal strain is a filamentous fungal strain. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal strain is a strain of a species of, but not limited to, *Acremonium, Aspergillus, Aureobasidium, Bjerkandera, Ceriporiopsis, Coprinus, Coriolus, Cryptococcus, Filibasidium, Fusarium, Humicola, Magnapoithe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma.*

In a most preferred embodiment, the filamentous fungal strain is an *Aspergillus aculeatus, Aspergillus awamori, Aspergillus foetidus, Aspergillus japonicus, Aspergillus nidulans, Aspergillus niger,* or *Aspergillus oryzae* strain. In another most preferred embodiment, the filamentous fungal strain is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum,*

*Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* strain. In an even most preferred embodiment, the filamentous fungal parent strain is a *Fusarium venenatum* (Nirenberg sp. nov.) strain. In another most preferred embodiment, the filamentous fungal strain is a a *Bjerkandera adusta, Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* strain.

Random Genomic Fragments

The term "random genomic fragment" is defined herein as a portion of the genome of a microbial strain.

Random genomic fragments may be prepared by isolating genomic DNA from a microbial strain using conventional methods and digesting the isolated genomic DNA with one or more suitable restriction enzymes for various periods of time to generate fragments. The digestions are then electrophoresed on an agarose gel to determine the size of the fragments. Gel slices containing fragments of a suitable size, e.g., 2 to 3 kb, are removed and the fragments are purified. The fragments are then ligated with a suitable vector digested with the same restriction enzyme. The ligation mixture is transformed into competent *E. coli* cells and transformants isolated on a selctable medium.

The term "random cDNA fragment" is defined herein as a segment of a sequence from a cDNA clone of an expressed eukaryotic gene.

Any other method known in the art may be used for generating random genomic fragments (see, for example, J. Sambrook, E. F. Fritsch, and T. Maniatus, 1989, *Molecular Cloning, A Laboratory Manual,* 2d edition, Cold Spring Harbor, NewYork).

Random cDNA fragments may be generated from eukaryotes as follows: Total polyadenylated mRNA is isolated from a eukaryote strain, e.g., filamentous fungus, and reverse transcribed into total cDNA. The total cDNA is digested with a restriction endonuclease, size-selected by agarose gel electrophoresis, isolated, and ligated into a vector, e.g., pZErO-2.1. The ligation mixture is transformed into competent *E. coli* cells and transformants are selected under selective pressure, e.g., kanamycin selection. The cDNA libraries isolated from the selected transformants are amplified, and isolated.

The term "random nucleic acid fragment" is defined herein as a random genomic or cDNA fragment, as defined above.

In the methods of the present invention, the random nucleic acid fragments are at least about 50 bp in length, preferably at least about 100 bp in length, more preferably at least about 500 bp in length, even more preferably at least about 1000 bp in length, most preferably at least about 1500 bp in length, and even most preferably at least about 2000 bp in length.

The random nucleic acid fragments may be obtained from the same strain as the strain from which the nucleic acid probes are derived. Alternatively, the strains may be different strains, for example, different species or different genera.

The random nucleic acid fragments may be obtained from any of the microorganisms described herein. In a preferred embodiment, the random nucleic acid fragments are obtained from *Bjerkandera adusta.* In another more preferred embodiment, the random nucleic acid fragments are obtained from *Bjerkandera adusta* ATCC 90940.

In another preferred embodiment, the random nucleic acid fragments are obtained from *Ceriporiopsis subvermispora.* In another more preferred embodiment, the random nucleic acid fragments are obtained from *Ceriporiopsis subvermispora* FPL 104807SS-5 (Forest Products Laboratory, Madison, Wis.).

In another preferred embodiment, the random nucleic acid fragments are obtained from *Fusarium venenatum.* In a more preferred embodiment, the random nucleic acid fragments are obtained from *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62–80 and O'Donnell et al., 1998, *Fungal Genetics and Biology* 23: 57–67; as well as taxonomic equivalents of *Fusarium venenatum* regardless of the species name by which they are currently known. In another more preferred embodiment, the *Fusarium venenatum* strain is a morphological mutant of *Fusarium venenatum* A3/5 or *Fusarium venenatum* ATCC 20334, as disclosed in WO 97/26330.

In another preferred embodiment, the random nucleic acid fragments are obtained from *Aspergillus niger.*

In another preferred embodiment, the random nucleic acid fragments are obtained from *Aspergillus oryzae.* In another more preferred embodiment, the random nucleic acid fragments are obtained from *Aspergillus oryzae* strain IFO 4177.

In another preferred embodiment, the random nucleic acid fragments are obtained from *Trichoderma reesei.* In another more preferred embodiment, the random nucleic acid fragments are obtained from *Trichoderma reesei* strain RutC-30 (Montenecourt and Eveleigh, 1979, *Adv. Chem. Ser.* 181: 289–301).

Microarrays

The term "an array of random nucleic acid fragments" is defined herein as a linear or two-dimensional array of preferably discrete elements of random nucleic acid fragments, each having a finite area, formed on the surface of a solid support.

The term "microarray" is defined herein as an array of random nucleic acid fragment elements having a density of discrete random nucleic acid fragment elements of at least about $100/cm^2$, and preferably at least about $1000/cm^2$. The random nucleic acid fragment elements in a microarray have typical dimensions, e.g., diameters, in the range of between about 10 to about 250 $\mu$m, preferably in the range of between about 10 to about 200 $\mu$m, more preferably in the range of between about 20 to about 150 $\mu$m, even more preferably in the range of between about 20 to about 100 $\mu$m, most preferably in the range of between about 50 to about 100 $\mu$m, and even most preferably in the range of between about 80 to about 100 $\mu$m, and are separated from other random nucleic acid fragment elements in the microarray by about the same distance.

Methods and instruments for forming microarrays on the surface of a solid support are well known in the art. See, for example, U.S. Pat. Nos. 5,807,522; 5,700,637; and 5,770,151. The instrument may be an automated device such as described in U.S. Pat. No. 5,807,522.

The term "a substrate containing an array of random nucleic acid fragments" is defined herein as a solid support having deposited on the surface of the support one or more of a plurality of random nucleic acid fragments for use in detecting binding of labeled nucleic acids to the random nucleic acid fragments.

The substrate may, in one aspect, be a glass support (e.g., glass slide) having a hydrophilic or hydrophobic coating on the surface of the support, and an array of distinct random nucleic acid fragments bound to the coating, where each distinct random nucleic acid fragment is disposed at a separate, defined position.

Each microarray in the substrate preferably contains at least $10^3$ distinct random nucleic acid fragments in a surface area of less than about 5 or 6 $cm^2$. Each distinct random nucleic acid fragment (i) is disposed at a separate, defined position in the array, (ii) has a length of at least 50 bp, and (iii) is present in a defined amount between about 0.1 femtomoles and 100 nanomoles or higher if necessary.

For a hydrophilic coating, the glass slide is coated by placing a film of a polycationic polymer with a uniform thickness on the surface of the slide and drying the film to form a dried coating. The amount of polycationic polymer added should be sufficient to form at least a monolayer of polymers on the glass surface. The polymer film is bound to the surface via electrostatic binding between negative silyl-OH groups on the surface and charged cationic groups in the polymers. Such polycationic polymers include, but are not limited to, polylysine and polyarginine.

Another coating strategy employs reactive aldehydes to couple DNA to the slides (Schena et al., 1996, *Proceedings of the National Academy of Science USA* 93: 10614–10619; Heller at al., 1997, *Proceedings of the National Academy of Science USA* 94: 2150–2155).

Alternatively, the surface may have a relatively hydrophobic character, i.e., one that causes aqueous medium deposited on the surface to bead. A variety of known hydrophobic polymers, such as polystyrene, polypropylene, or polyethylene, have desirable hydrophobic properties, as do glass and a variety of lubricant or other hydrophobic films that may be applied to the support surface. A support surface is "hydrophobic" if an aqueous droplet applied to the surface does not spread out substantially beyond the area size of the applied droplet, wherein the surface acts to prevent spreading of the droplet applied to the surface by hydrophobic interaction with the droplet.

In another aspect, the substrate may be a multi-cell substrate where each cell contains a microarray of random nucleic acid fragments, and preferably an identical microarray, formed on a porous surface. For example, a 96-cell array may typically have array dimensions between about 12 and 244 mm in width and 8 and 400 mm in length, with the cells in the array having width and length dimension of 1/12 and 1/8 the array width and length dimensions, respectively, i.e., between about 1 and 20 in width and 1 and 50 mm in length.

The solid support may include a water-impermeable backing such as a glass slide or rigid polymer sheet, or other non-porous material. Formed on the surface of the backing is a water-permeable film, which is formed of porous material. Such porous materials include, but are not limited to, nitrocellulose membrane nylon, polypropylene, and polyvinylidene difluoride (PVDF) polymer. The thickness of the film is preferably between about 10 and 1000 $\mu$m. The film may be applied to the backing by spraying or coating, or by applying a preformed membrane to the backing.

Alternatively, the solid support may be simply a filter composed of nitrocellulose, nylon, polypropylene, or polyvinylidene difluoride (PVDF) polymer, or for that matter any material suitable for use.

The film surface may be partitioned into a desirable array of cells by water-impermeable grid lines typically at a distance of about 100 to 2000 $\mu$m above the film surface. The grid lines can be formed on the surface of the film by laying down an uncured flowable resin or elastomer solution in an array grid, allowing the material to infiltrate the porous film down to the backing, and then curing the grid lines to form the cell-array substrate.

The barrier material of the grid lines may be a flowable silicone, wax-based material, thermoset material (e.g., epoxy), or any other useful material. The grid lines may be applied to the solid support using a narrow syringe, printing techniques, heat-seal stamping, or any other useful method known in the art.

Each well preferably contains a microarray of distinct random nucleic acid fragments. "Distinct random nucleic acid fragments" as applied to the nucleic acid fragments forming a microarray is defined herein as an array member which is distinct from other array members on the basis of a different random nucleic acid fragment sequence, and/or different concentrations of the same or distinct nucleic acid fragments, and/or different mixtures of distinct nucleic acid fragments or different-concentrations of nucleic acid fragments. Thus an array of "distinct random nucleic acid fragments" may be an array containing, as its members, (i) distinct nucleic acid fragments, which may have a defined amount in each member, (ii) different, graded concentrations of given-sequence nucleic acid fragments, and/or (iii) different-composition mixtures of two or more distinct nucleic acid fragments.

However, any type of substrate known in the art may be used in the methods of the present invention.

The delivery of a known amount of a selected random nucleic acid fragment to a specific position on the support surface is preferably performed with a dispensing device equipped with one or more tips for insuring reproducible deposition and location of the random nucleic acid fragments and for preparing multiple arrays. Any dispensing device known in the art may be used in the methods of the present invention. See, for example, U.S. Pat. No. 5,807, 522.

For liquid-dispensing on a hydrophilic surface, the liquid will have less of a tendency to bead, and the dispensed volume will be more sensitive to the total dwell time of the dispenser tip in the immediate vicinity of the support surface.

For liquid-dispensing on a hydrophobic surface, flow of fluid from the tip onto the support surface will continue from the dispenser onto the support surface until it forms a liquid bead. At a given bead size, i.e., volume, the tendency of liquid to flow onto the surface will be balanced by the hydrophobic surface interaction of the bead with the support surface, which acts to limit the total bead area on the surface, and by the surface tension of the droplet, which tends toward a given bead curvature. At this point, a given bead volume will have formed, and continued contact of the dispenser tip with the bead, as the dispenser tip is being withdrawn, will have little or no effect on bead volume.

The desired deposition volume, i.e., bead volume, formed is preferably in the range 2 pl (picoliters) to 2 nl (nanoliters), although volumes as high as 100 nl or more may be dispensed. It will be appreciated that the selected dispensed volume will depend on (i) the "footprint" of the dispenser tip(s), i.e., the size of the area spanned by the tip(s), (ii) the hydrophobicity of the support surface, and (iii) the time of contact with and rate of withdrawal of the tip(s) from the support surface. In addition, bead size may be reduced by increasing the viscosity of the medium, effectively reducing the flow time of liquid from the dispensing device onto the support surface. The drop size may be further constrained by depositing the drop in a hydrophilic region surrounded by a hydrophobic grid pattern on the support surface.

At a given tip size, bead volume can be reduced in a controlled fashion by increasing surface hydrophobicity, reducing time of contact of the tip with the surface, increasing rate of movement of the tip away from the surface, and/or increasing the viscosity of the medium. Once these parameters are fixed, a selected deposition volume in the desired picoliter to nanoliter range can be achieved in a repeatable fashion.

After depositing a liquid droplet of a random nucleic acid fragment sample at one selected location on a support, the tip may be moved to a corresponding position on a second support, the random nucleic acid fragment sample is deposited at that position, and this process is repeated until the random nucleic acid fragment sample has been deposited at a selected position on a plurality of supports.

This deposition process may then be repeated with another random nucleic acid fragment sample at another microarray position on each of the supports.

The diameter of each random nucleic acid fragment region is preferably between about 20–200 µm. The spacing between each region and its closest (non-diagonal) neighbor, measured from center-to-center, is preferably in the range of about 20–400 µm. Thus, for example, an array having a center-to-center spacing of about 250 µm contains about 40 regions/cm or 1,600 regions/cm$^2$. After formation of the array, the support is treated to evaporate the liquid of the droplet forming each region, to leave a desired array of dried, relatively flat random nucleic acid fragment regions. This drying may be done by heating or under vacuum. The DNA can also be UV-crosslinked to the polymer coating.

Nucleic Acid Probes

In the methods of the present invention, the strains are cultivated in a nutrient medium with and without a substrate using methods well known in the art for isolation of nucleic acids to be used as probes. For example, the strains may be cultivated by shake flask cultivation, small-scale or large-scale fermentation (including continuous, batch, fed-batch, or solid state fermentations) in laboratory or industrial fermentors performed in a suitable medium. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

The nucleic acid probes from the microbial strains cultured on medium with and without substrate may be any nucleic acid including genomic DNA, cDNA, and RNA, and may be isolated using standard methods known in the art. For example, cDNA probes may be obtained from total RNA isolated from the strains using standard methods and reverse transcribed into total cDNA.

The populations of isolated nucleic acid probes may be labeled with calorimetric, radioactive (for example, $^{32}$P, $^{33}$P, or $^{35}$S), fluorescent reporters, or other reporters using methods known in the art (Chen et al., 1998, *Genomics* 51: 313–324; DeRisi et al., 1997, *Science* 278: 680–686; U.S. Pat. No. 5,770,367).

In a preferred embodiment, the probes are labeled with fluorescent reporters. For example, the cDNA probes may be labeled during reverse transcription from the respective RNA pools by incorporation of fluorophores as dye-labeled nucleotides (DeRisi et al., 1997, supra), e.g., Cy5-labeled deoxyuridine triphosphate, or the isolated cDNAs may be directly labeled with different fluorescent functional groups. Fluorescent-labeled nucleotides include, but are not limited to, fluorescein conjugated nucleotide analogs (green fluorescence), lissamine nucleotide analogs (red fluorescence). Fluorescent functional groups include, but are not limited to, Cy3 (a green fluorescent dye) and Cy5 (red fluorescent dye).

Array Hybridization

The labeled nucleic acids from the two strain cultivated with and without substrate are then added to an array of random nucleic acid fragments under conditions where the nucleic acid pools from the two strains hybridize to complementary sequences of the random nucleic acid fragments in the array. For purposes of the present invention, hybridization indicates that the labeled nucleic acids from the two strains hybridize to the random nucleic acid fragments under very low to very high stringency conditions.

A small volume of the labeled nucleic acids mixture is loaded onto the substrate. The solution will spread to cover the entire microarray. In the case of a multi-cell substrate, one or more solutions are loaded into each cell which stop at the barrier elements.

For nucleic acid probes of at least about 100 nucleotides in length, miroarray hybridization conditions described by Eisen and Brown, 1999, *Methods of Enzymology* 303: 179–205, may be used. Hybridization is conducted under a cover slip at 65° C. in 3×SSC for 4–16 hours followed by post-hybridization at room temperature after removal of the cover slip in 2×SSC, 0.1% SDS by plunging the array two or three times in the solution, followed by successive washes in 1×SSC for 2 minutes and 0.2×SSC wash for two or more minutes.

Conventional conditions of very low to very high stringency conditions may also be used. Very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures.

The carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For shorter nucleic acid probes which are less than 50 nucleotides, microarray hybridization conditions described by Kane et a/., 2000, *Nucleic Acids Research* 28: 4552–4557, may be used. Hybridization is conducted under a supported coverslip at 42° C. for 16–18 hours at high humidity in 50% formamide, 4.1× Denhardts, 4.4×SSC, and 100 µg/ml of herring sperm DNA. Arrays are washed after removal of the coverslip in 4×SSC by immersion into 1×SSC, 0.1% SDS for 10 minutes, 0.1×SSC, 0.1% SDS twice for 10 minutes, and 0.1×SSC twice for 10 minutes.

For shorter nucleic acid probes which are about 50 nucleotides to about 100 nucleotides in length, conventional stringency conditions may be used. Such stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

The carrier material is finally washed once in 6×SSC plus 0.1% SDS for 15 minutes and twice each for 15 minutes using 6×SSC at 5° C. to 10° C. below the calculated $T_m$.

The choice of hybridization conditions will depend on the degree of homology between the random nucleic acid fragments and the nucleic acid probes obtained from the strain cultured with and without substrate. For example, where the nucleic acid probes and the random nucleic acid fragments are obtained from identical strains, high stringency conditions may be most suitable. Where the strains are from a genus or species different from which the random nucleic acid fragments were obtained, low or medium stringency conditions may be more suitable.

In a preferred embodiment, the hybridization is conducted under low stringency conditions. In a more preferred embodiment, the hybridization is conducted under medium stringency conditions. In a most preferred embodiment, the hybridization is conducted under high stringency conditions.

The entire solid support is then reacted with detection reagents if needed and analyzed using standard calorimetric, radioactive, or fluorescent detection means. All processing and detection steps are performed simultaneously to all of the microarrays on the solid support ensuring uniform assay conditions for all of the microarrays on the solid support.

Detection

The most common detection method is laser-induced fluorescence detection using confocal optics (Cheung et al., 1998, Nat Genet 18: 225–230). The array is examined under fluorescence excitation conditions such that (i) the random nucleic acid fragments in the array that hybridize to the first nucleic acid probes obtained from the strain cultured without substrate and to the second nucleic acid probes obtained from the strain cultured with substrate produce a distinct first fluorescence emission color and a distinct second fluorescence emission color, respectively, and (ii) the random nucleic acid fragments in the array that hybridize to substantially equal numbers of nucleic acid probes obtained from the strain cultured without substrate and from the strain cultured with substrate produce a distinct combined fluorescence emission color; wherein the relative expression of the genes in the strains can be determined by the observed fluorescence emission color of each spot in the array.

The fluorescence excitation conditions are based on the selection of the fluorescence reporters. For example, Cy3 and Cy5 reporters are detected with solid state lasers operating at 532 nm and 632 nm, respectively.

Other methods of detection may be used employing calorimetric and radioactive (for example, $^{32}P$, $^{33}P$, or $^{35}S$) reporters, or other reporters using methods known in the art (Chen et al., 1998, supra; DeRisi et al., 1997, supra; U.S. Pat. No. 5,770,367).

Data Analysis

The fluorescence data obtained from the scanned image may then be analyzed using any of the commercially available image analysis software. The software preferably identifies array elements, subtracts backgrounds, deconvolutes multi-color images, flags or removes artifacts, verifies that controls have performed properly, and normalizes the signals (Chen et al., 1997, Journal of Biomedical Optics 2: 364–374).

Several computational methods have been described for the analysis and interpretation of microarray-based expression profiles including cluster analysis (Eisen et al., 1998, Proc. Nat. Acad. Sci. USA 95: 14863–14868), parametric ordering of genes (Spellman et al., 1998, Mol. Biol. Cell 9: 3273–3297), and supervised clustering methods based on representative hand-picked or computer-generated expression profiles (Chu et al., 1998. Science 282: 699–705).

Isolation of Genes

Random nucleic acid fragments containing genes identified to be induced by the present of substrate in the medium are characterized by determining the sequence of the fragment. Based on the sequence, the gene can then be isolated using methods well known in the art.

The techniques used to isolate or clone a gene include isolation from genomic DNA, preparation from cDNA, or a combination thereof. The cloning of the gene from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleic acid sequence-based amplification (NASBA) may be used. The gene may be cloned from the strain of interest, or another or related organism and thus, for example, may be an allelic or species variant of the gene.

Nucleic Acid Constructs

The present invention also relates to nucleic acid constructs comprising a gene isolated according to the methods describe herein, wherein the gene is operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence which directly specifies the amino acid sequence of its protein product. The boundaries of a genomic coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a gene of interest isolated according to the present invention. Each control sequence may be native or foreign to the gene. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the gene. The term "operably linked" is defined herein as a configuration in which a control sequence is appropriately placed at a position relative to the coding sequence of the gene such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyA), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the gene. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the gene may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be to required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57:109–137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of the polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the gene of interest would be operably linked with the regulatory sequence.

Expression Vectors

The present invention also relates to recombinant expression vectors comprising a gene isolated according to the methods described herein, a promoter, and transcriptional and translational stop signals. The various nucleic acid and control sequences described above may be joined together to produce a recombinant expression vector which may include one or more convenient restriction sites to allow for insertion or substitution of the gene encoding the polypeptide at such sites. Alternatively, the gene may be expressed by inserting it or a nucleic acid construct comprising the gene into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the gene of interest. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors preferably contain an element(s) that permits integration of the vector into the host cell's genome or autonomous replication of the vector in the cell independent of the genome.

For integration into the host cell genome, the vector may rely on the nucleic acid sequence of the gene or any other element of the vector for integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a gene isolated according to the present invention may be inserted into the host cell to increase production of the gene product. An increase in the copy number of the gene can be obtained by integrating at least one additional copy of the gene into the host cell genome or by including an amplifiable selectable marker gene with the gene where cells containing amplified copies of the selectable marker gene, and thereby additional copies of the gene of interest, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

Host Cells

The present invention also relates to recombinant host cells, comprising a gene isolated according to method described herein, which are advantageously used in the recombinant production of the polypeptides having biological activity. A vector comprising a gene is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene and its source.

The host cell may be a unicellular microorganism, e.g., a prokaryote, or a non-unicellular microorganism, e.g., a eukaryote.

Useful unicellular cells are those bacterial cells described herein.

The introduction of a vector into a bacterial host cell may, for instance, be effected by protoplast transformation (see, e.g., Chang and Cohen, 1979, *Molecular General Genetics* 168: 1111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

The host cell may be a eukaryote, such as a mammalian, insect, plant, or fungal cell as described herein.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming *Fusarium* species are described by Malardier et al., 1989, *Gene* 78: 147–156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide having biological activity comprising (a) cultivating a host cell under conditions suitable for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J. -C. Janson and Lars Ryden, editors, VCH Publishers, New York, 1989).

The present invention also relates to isolated enzymes encoded by genes isolated using the methods described herein.

Polypeptides Having Peroxidase Activity

The term "peroxidase activity" is defined herein as an oxidation-reduction activity that catalyzes the oxidation of a suitable reducing substrate ($H^+$donor) by hydrogen peroxide through the formation of a heme intermediate. When the reducing substrate is Mn(II) ion, the peroxidase activity is then specified as manganese peroxidase activity.

For purposes of the present invention, peroxidase activity is measured according to the procedure described by Mester and Field, 1998, *Journal of Biological Chemistry* 273: 15412–15417, where the oxidation of Mn(II) is monitored by the formation of Mn(III)-malonate complex at 270 nm or by the secondary oxidation of phenol red with Mn(II) at 600 nm and pH 4.5. Peroxidase activity may also be measured by monitoring the oxidation of 2,6-dimethoxyphenol to coerulignone, ABTS to ABTS+, and veratryl alcohol to veratraldehyde at 469, 420, and 310 nm, respectively, and pH 7.0. One unit of peroxidase activity is defined as 1.0 μmole of hydrogen peroxidase consumed per minute at 25° C., pH 4.5 or pH 7.

In a first embodiment, the present invention relates to isolated polypeptides having an amino acid sequence which has a degree of identity to amino acids 19 to 316 of SEQ ID NO:2 (i.e., the mature polypeptide) of at least about 85%, preferably at least about 90%, more preferably at least about 95%, and most preferably at least about 97%, which have peroxidase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 19 to 316 of SEQ ID NO:2. For purposes of the present invention, the degree of identity between two amino acid sequences is determined by the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

Preferably, the polypeptides of the present invention comprise the amino acid sequence of SEQ ID NO:2 or an allelic variant thereof; or a fragment thereof that has peroxidase activity. In a more preferred embodiment, the polypeptide of the present invention comprises the amino acid sequence of SEQ ID NO:2. In another preferred embodiment, the polypeptide of the present invention comprises amino acids 19 to 316 of SEQ ID NO:2, or an allelic variant thereof; or a fragment thereof that has peroxidase activity. In another preferred embodiment, the polypeptide of the present invention comprises amino acids 19 to 316 of SEQ ID NO:2. In another preferred embodiment, the polypeptide of the present invention consists of the amino acid sequence of SEQ ID NO:2 or an allelic variant thereof; or a fragment thereof that has peroxidase activity. In another preferred embodiment, the polypeptide of the present invention consists of the amino acid sequence of SEQ ID NO:2. In another preferred embodiment, the polypeptide consists of amino acids 19 to 316 of SEQ ID NO:2 or an allelic variant thereof; or a fragment thereof that has peroxidase activity. In another preferred embodiment, the polypeptide consists of amino acids 19 to 316 of SEQ ID NO:2.

A fragment of SEQ ID NO:2 is a polypeptide having one or more amino acids deleted from the amino and/or carboxyl terminus of this amino acid sequence. Preferably, a fragment contains at least 240 amino acid residues, more preferably at least 260 amino acid residues, and most preferably at least 280 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In a second embodiment, the present invention relates to isolated polypeptides having peroxidase activity which are encoded by nucleic acid sequences which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) nucleotides 55 to 1249 of SEQ ID NO:1, (ii) the genomic sequence comprising or cDNA sequence contained in nucleotides 55 to 1249 of SEQ ID NO:1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, NewYork). The subsequence of SEQ ID NO:1 may be at least 100 nucleotides or preferably at least 200 nucleotides. Moreover, the subsequence may encode a polypeptide fragment which has peroxidase activity. The polypeptides may also be allelic variants or fragments of the polypeptides that have peroxidase activity.

The nucleic acid sequence of SEQ ID NO:1 or a subsequence thereof, as well as the amino acid sequence of SEQ ID NO:2 or a fragment thereof, may be used to design a nucleic acid probe to identify and clone DNA encoding polypeptides having peroxidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA or cDNA library prepared from such other organisms may be screened for DNA which hybridizes with the probes described above and which encodes a polypeptide having peroxidase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO:1, its complementary strand, or a subsequence thereof, under very low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO:2, or a subsequence thereof. In another preferred embodiment, the nucleic acid probe is SEQ ID NO:1. In another preferred embodiment, the nucleic acid probe is the mature polypeptide coding region of SEQ ID NO:1. In another preferred embodiment, the nucleic acid probe is the nucleic acid sequence contained in plasmid pCsubHP1F which is contained in *Escherichia coli* NRRL B-30561, wherein the nucleic acid sequence encodes a polypeptide having peroxidase activity. In another preferred embodiment, the nucleic acid probe is the mature polypeptide coding region contained in plasmid pCsubHP1 F which is contained in *Escherichia coli* NRRL B-30561.

For long probes of at least 100 nucleotides in length, very low to very high stringency conditions are defined as prehybridization and hybridization at 42° C. in 5× SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC , 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6× SCC plus 0.1% SDS for 15 minutes and twice each for 15 minutes using 6×SSC at 5° C. to 10° C. below the calculated $T_m$.

In a third embodiment, the present invention relates to variants of the polypeptide having an amino acid sequence of SEQ ID NO:2 comprising a substitution, deletion, and/or insertion of one or more amino acids.

The amino acid sequences of the variant polypeptides may differ from the amino acid sequence of SEQ ID NO:2 or the mature polypeptide thereof by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a fourth embodiment, the present invention relates to isolated polypeptides having immunochemical identity or partial immunochemical identity to the polypeptide having the amino acid sequence of SEQ ID NO:2 or the mature polypeptide thereof. The immunochemical properties are determined by immunological cross-reaction identity tests by the well-known Ouchterlony double immunodiffusion procedure. Specifically, an antiserum containing polyclonal antibodies which are immunoreactive or bind to epitopes of the polypeptide having the amino acid sequence of SEQ ID NO:2 or the mature polypeptide thereof are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual*, Cold Spring Harbor Press, Cold Spring Harbor, NewYork The polypeptides of the present invention have at least 20%, preferably at least 40%, more preferably at least 60%, even more preferably at least 80%, even more preferably at least 90%, and most preferably at least 100% of the peroxidase activity of the mature polypeptide of SEQ ID NO:2.

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide is secreted extracellularly.

A polypeptide of the present invention may be a bacterial polypeptide. For example, the polypeptide may be a gram positive bacterial polypeptide such as a *Bacillus* polypeptide, e.g., a *Bacillus alkalophilus*, *Bacillus amyloliquefaciens*, *Bacillus brevis*, *Bacillus circulans*, *Bacillus coagulans*, *Bacillus lautus*, *Bacillus lentus*, *Bacillus licheniformis*, *Bacillus megaterium*, *Bacillus stearothermophilus*, *Bacillus subtilis*, or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may be a fungal polypeptide, and more preferably a yeast polypeptide such as a *Candida*, *Kluyveromyces*, *Pichia*, *Saccharomyces*, *Schizosaccharomyces*, or *Yarrowia* polypeptide; or more preferably a filamentous fungal polypeptide such as an *Acremonium*, *Aspergillus*, *Aureobasidium*, *Bjerkandera*, *Ceriporiopsis*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* polypeptide.

In a preferred embodiment, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* polypeptide.

In another preferred embodiment, the polypeptide is an *Aspergillus aculeatus*, *Aspergillus awamori*, *Aspergillus foetidus*, *Aspergillus japonicus*, *Aspergillus nidulans*, *Aspergillus niger*, *Aspergillus oryzae*, *Bjerkandera adusta*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* polypeptide.

In another preferred embodiment, the polypeptide is a *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, or *Ceriporiopsis subvermispora* polypeptide.

In a more preferred embodiment, the polypeptide is a *Ceriporiopsis subvermispora* polypeptide, and most preferably a *Ceriporiopsis subvermispora* FPL 104807SS-5 (Forest Products Laboratory, Madison, Wis.) polypeptide, e.g., the polypeptide with the amino acid sequence of SEQ ID NO: 2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-peroxidase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences Encoding Polypeptides Having Peroxidase Activity

The present invention also relates to isolated nucleic acid sequences which encode a polypeptide having peroxidase activity of the present invention. In a preferred embodiment, the nucleic acid sequence is set forth in SEQ ID NO:1. In another more preferred embodiment, the nucleic acid sequence is the sequence contained in plasmid pCsubHP1F that is contained in *Escherichia coli* NRRL B-30561. In another preferred embodiment, the nucleic acid sequence is the mature polypeptide coding region of SEQ ID NO:1. In another more preferred embodiment, the nucleic acid sequence is the mature polypeptide coding region contained in plasmid pCsubHP1F that is contained in *Escherichia coli* NRRL B-30561. The present invention also encompasses nucleic acid sequences which encode a polypeptide having the amino acid sequence of SEQ ID NO:2 or the mature polypeptide thereof, which differ from SEQ ID NO:1 by virtue of the degeneracy of the genetic code. The present invention also relates to subsequences of SEQ ID NO:1 which encode fragments of SEQ ID NO:2 that have peroxidase activity.

A subsequence of SEQ ID NO:1 is a nucleic acid sequence encompassed by SEQ ID NO:1 except that one or more nucleotides from the 5' and/or 3' end have been deleted. Preferably, a subsequence contains at least 720 nucleotides, more preferably at least 780 nucleotides, and most preferably at least 840 nucleotides.

The present invention also relates to mutant nucleic acid sequences comprising at least one mutation in the mature polypeptide coding sequence of SEQ ID NO:1, in which the mutant nucleic acid sequence encodes a polypeptide which consists of amino acids 19 to 316 of SEQ ID NO:2.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of *Ceriporiopsis,* or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the mature polypeptide coding sequence of SEQ ID NO:1 (i.e., nucleotides 55 to 1249) of at least about 85%, preferably about 90%, more preferably about 95%, and most preferably about 97% homology, which encode an active polypeptide having peroxidase activity. For purposes of the present invention, the degree of homology between two nucleic acid sequences is determined by the Wilbur-Lipman method (Wilbur and Lipman, 1983, *Proceedings of the National Academy of Science USA* 80: 726–730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=3, gap penalty=3, and windows=20.

Modification of a nucleic acid sequence encoding a polypeptide having peroxidase activity of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for peroxidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

The present invention also relates to isolated nucleic acid sequences encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with the nucleic acid sequence of SEQ ID NO:1 or its complementary strand; or allelic variants and subsequences thereof (Sambrook et al., 1989, supra), as defined herein.

The present invention also relates to isolated nucleic acid sequences produced by (a) hybridizing a DNA under very low, low, medium, medium-high, high, or very high stringency conditions with (i) nucleotides 55 to 1249 of SEQ ID NO:1, (ii) the genomic sequence comprising or cDNA sequence contained in nucleotides 55 to 1249 of SEQ ID NO:1, (iii) a subsequence of (i) or (ii), or (iv) a complementary strand of (i), (ii), or (iii); and (b) isolating the nucleic acid sequence. The subsequence is preferably a sequence of at least 100 nucleotides such as a sequence which encodes a polypeptide fragment which has peroxidase activity.

Nucleic Acid Constructs, Vectors, and Host Cells Comprising Nucleic Acid Sequences Encoding Polypeptides Having Peroxidase Activity The present invention also relates to nucleic acid constructs comprising a nucleic acid sequence encoding a polypeptide having peroxidase activity, and vectors and host cells thereof. The nucleic acid constructs, vectors, and host cells can be constructed as described herein.

Methods of Production of Polypeptides Having Peroxidase Activity

The present invention also relates to methods for producing a polypeptide having peroxidase of the present invention comprising (a) cultivating a strain, which in its wild-type form is capable of producing the polypeptide, to produce the polypeptide; and (b) recovering the polypeptide. Preferably, the strain is of the genus *Ceriporiopsis,* and more preferably *Ceriporiopsis subvermispora.*

The present invention also relates to methods for producing a polypeptide having peroxidase activity of the present invention comprising (a) cultivating a host cell under conditions conducive for production of the polypeptide; and (b) recovering the polypeptide.

These methods of production are described herein.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

Compositions

In a still further aspect, the present invention relates to compositions comprising a polypeptide having peroxidase of the present invention. Preferably, the compositions are enriched in a polypeptide of the present invention. In the present context, the term "enriched" indicates that the peroxidase activity of the composition has been increased, e.g., with an enrichment factor of 1.1.

The composition may comprise a polypeptide of the invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be producible by means of a microorganism belonging to the genus *Aspergillus,* preferably *Aspergillus aculeatus, Aspergillus awamori, Aspergillus niger,* or *Aspergillus oryzae,* or *Trichoderma, Humicola,* preferably *Humicola insolens,* or *Fusarium,* preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum.*

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having peroxidase activity.

The peroxidases can be used in number of different industrial processes. One process includes polymerization of lignin, both Kraft and lignosulfates, in order to produce a lignin with a higher molecular weight. A neutral/alkaline peroxidase is a particular advantage in that Kraft lignin is more soluble at higher pHs. Such methods are described in, for example, Jin et al., 1991, *Holzforschung* 45: 467–468; U.S. Pat. No. 4,432,921; EP 0 275 544; PCT/DK93/00217, 1992. Peroxidase is also useful in the copolymerization of lignin with low molecular weight compounds, such as is described by Milstein et al., 1994, *Appl. Microbiol. Biotechnology* 40: 760–767.

The peroxidases of the present invention can also be used for in-situ depolymerization of lignin in Kraft pulp, thereby producing a pulp with lower lignin content. This use of peroxidase is an improvement over the current use of chlorine for depolymerization of lignin, which leads to the production of chlorinated aromatic compounds, which are an environmentally undesirable by-product of paper mills. Such uses are described in, for example, *Current Opinion in Biotechnology* 3: 261–266, 1992; *Journal of Biotechnology* 25: 333–339, 1992; Hiroi et al., *Svensk Papperstidning* 5:162–166, 1976.

Oxidation of dyes or dye precursors and other chromophoric compounds leads to decolorization of the compounds. Peroxidase can be used for this purpose, which can be particularly advantageous in a situation in which a dye transfer between fabrics is undesirable, e.g., in the textile industry and in the detergent industry. Methods for dye transfer inhibition and dye oxidation can be found in WO 92/01406; WO 92/18683; WO 92/18687; WO 91/05839; EP 0495836; Calvo, 1991, *Medededelingen van de Faculteit Landbouw-wetenschappen/Rijiksuniversitet Gent* 56: 1565–1567; Tsujino et al., 1991, *J. Soc. Chem.* 42: 273–282. Use of peroxidase in oxidation of dye precursors for hair dyeing is disclosed in U.S. Pat. No. 3,251,742, the contents of which are incorporated herein by reference.

The present peroxidases can also be used for the polymerization or oxidation of phenolic compounds present in liquids. An example of such utility is the treatment of juices, such as apple juice, so that the peroxidase will accelerate a precipitation of the phenolic compounds present in the juice, thereby producing a more stable juice. Such applications have been described in Stutz, 1993, *Fruit Processing* 7/93, 248–252; Maier et al., 1990, Dt Lebensmittel-rindschau 86: 137–142; Dietrich et al., 1990, Fluss. Obst 57: 67–73.

Peroxidases of the present invention are also useful in soil detoxification (Nannipieri et al., 1991, *J. Environ. Qual.* 20: 510–517; Dec and Bollag, 1990, *Arch. Environ. Contam. Toxicol.* 19: 543–550).

Signal Peptide

The present invention also relates to nucleic acid constructs comprising a gene encoding a protein operably linked to a nucleic acid sequence consisting of nucleotides 1 to 54 of SEQ ID NO:1 encoding a signal peptide consisting of amino acids 1 to 18 of SEQ ID NO:2, wherein the gene is foreign to the nucleic acid sequence.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The nucleic acid sequence may be operably linked to foreign genes with other control sequences. Such other control sequences are described supra.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred embodiment, the protein is an oxidoreductase, transferase, hydrolase, lyase, isomerase, or ligase. In an even more preferred embodiment, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Chemicals used as buffers and substrates were commercial products of at least reagent grade.

Example 1

Isolation of Genomic DNA from *Ceriporiopsis subvermispora*

A quarter inch square of agar of *Ceriporiopsis subvermispora* FPL 104807SS-5 (Forest Products Laboratory, Madison, Wis.) mycelia from a PDA plate were inoculated into 250 ml of YEG medium and incubated at 28° C. for 5 days. The mycelia were harvested by filtration through Miracloth (Calbiochem, San Diego, Calif.) and were frozen quickly in liquid nitrogen. DNA was isolated as described previously (Walheitner et al., 1996, *Current Genetics* 29: 395–403). The DNA pellet was resuspended in 500 µl of TE buffer (10 mM Tris-1 mM EDTA), and 5 µl was electrophoresed on a 1% agarose gel to confirm the quality of the preparation.

Example 2

Construction of a *Ceriporiopsis subvermispora* Genomic Library

A total of 30 µg of *Ceriporiopsis subvermispora* genomic DNA was digested with Tsp509I (New England Biolabs, Beverly, Mass.) in a total volume of 150 µl using the manufacturer's recommended conditions. Aliquots of 30 µl of the digested DNA were removed at 10, 11, 12, 14, and 16 minutes after the addition of Tsp509I. The digestions were electrophoresed on a 0.8% agarose gel using TAE buffer (4.84 g of Tris Base, 1.14 ml of glacial acetic acid, and 2 ml of 0.5 M EDTA pH 8.0 per liter). A large gel slice containing the 2 to 3 kb digested DNA was removed, and the fragments were purified using β-agarase (New England Biolabs, Beverly, Mass.) following the manufacturer's protocols.

A total of 3 µg of pUC19 was digested with EcoRI and treated with shrimp alkaline phosphatase (Amersham Pharmacia Biotech, Arlington Heights, Ill.) following the manufacturer's protocols. The digested DNA was electrophoresed on a 0.8% agarose gel using TAE buffer, and the gel slice containing the linearized plasmid was excised from the gel. The plasmid DNA was isolated from the gel slice using a Qiaquick spin column (QIAGEN, Chatsworth, Calif.).

The 2–3 kb Tsp509I genomic or cDNA fragments and the EcoRI digested pUC19 were ligated together overnight at room temperature with T4 DNA ligase (New England Biolabs, Beverly, Mass.). The ligation reaction was precipitated by adding 1/10 volume of 3 M sodium acetate pH 5.0 and 2.5 volumes of 95% ethanol, incubating on ice for 30 minutes, and centrifuging at 12,000×g for 30 minutes. The ligated DNA was resuspended in 10 µl of TE buffer.

Three 40 µl aliquots of *E. coli* Electromax DH10B competent cells (Gibco BRL, Bethesda, Md.) were transformed by electroporation with a time constant of 2.3 at 2.5 kV, 25 µF, 100Ω in a 0.1 cm cuvette and 1 µl of the ligated DNA. After transformation the cells were centrifuged at 1660×g for 5 to 10 minutes. The supernatant was carefully removed and the pelleted cells were resuspended in 0.5 ml of 2×LB medium plus 0.5 ml of 50% sterile glycerol. LB medium (pH 7.4) is composed per liter of 10 g of bacto-tryptone, 5 g of yeast extract, and 10 g of NaCl. The cells were frozen quickly in a dry ice ethanol bath. The aliquots were then frozen at −80° C.

The three transformations were titered after 1 day at −80° C. by plating on LB plates supplemented with ampicillin. The total number of independent transformants were 23,000, 32,500, and 34,500 per transformation. The frozen glycerol stocks were sent to Genome Systems (St. Louis, Mo.) for colony picking. A library of approximately 50,000 in 384-well plates was obtained.

Example 3

Isolation of RNA from *Ceriporiopsis subvermispora* Cultures for Probes

Six 1 liter flasks with 29 ml of basal minimal medium (Rüttimann et al., 1992, *Biotechnology and Applied Biochemistry* 16: 64–76) were incubated with agar plugs from a PDA plate containing *Ceriporiopsis subvermispora* mycelia. The basal minimal medium contained per liter 10 g of glucose, 1 mM ammonium tartrate, 10 mM transaconitic acid (pH 4.5), 2 g of $KH_2PO_4$, 0.5 g of $MgSO_4 \cdot 7H_2O$, 0.1 g of $CaCl_2 \cdot 2H_2O$, 1 mg of thiamine hydrochloride, and 1 ml of trace element solution. Trace elements contained per liter 15 g of nitroacetic acid, 1 g of $FeSO_4 \cdot 7H_2O$, 1.89 of $CoCl_2 \cdot 6H_2O$, 1 g of $ZnCl_2 \cdot 7H_2O$, 0.07 g of $Al_2(SO_4)_3 \cdot 18 H_2O$, 0.1 g of Cu $SO_4 \cdot 5H_2O$, 0.1 g of $H_3BO_3$, 0.1 g of $NaMoO_4 \cdot 2H_2O$, 30 g of $MgSO_4 \cdot 7H_2O$, 10 g of NaCl, 0.82 g of $CaCl_2$, and 0.5 g of $MnSO_4$. The flasks were incubated at 28° C. without shaking for 15 days. The mycelia mats were harvested from the flasks and homogenized in sterile water in a Waring blender for 15 seconds three times with 30 second intervals to prevent the mycelia from warming. The homogenized mycelia were added to a 1 liter flask containing 20 gm of hardwood thermomechanical pulp that had previously been processed in a Waring blender for 30 seconds, and the mixture was stirred. For the minimal medium cultures, the homogenized mycelia were added to 15 ml of minimal medium in 1 liter flasks. The cultures were incubated at 30° C. for 30 days without shaking and the entire pulp culture containing pulp plus mycelia was frozen quickly in liquid nitrogen. The mycelia from the minimal medium culture were harvested by filtration through Miracloth and quickly frozen in liquid nitrogen.

RNA was prepared from the culture using a phenol/chloroform extraction. Fresh p-aminosalicylic (PAS) (Sigma Chemical Co., St. Louis, Mo.) solution was prepared by mixing 9.6 gm in 80 ml of diethylpyrocarbonate (DEP)-treated water (Amresco, Solon, Ohio). Fresh tri-isopropyinaphthalene sulfonic acid (TNS) solution was prepared by mixing 1.6 gm in 80 ml DEP-treated water. 5×RNB was prepared by adding 24.2 g of Tris-HCl, 14.6 g of NaCl and 19 of EGTA to 200 ml of DEP-treated water and adjusting the pH to 8.5 with NaOH. RNA extraction buffer was prepared by adding the PAS solution to the TNS solution while stirring. The PAS/TNS mixture was then added to 40 ml of RNB while stirring, and the final solution was placed on ice. The frozen mycelia or mycelia plus pulp were ground to a fine powder in a coffee grinder that was prechilled with a few chips of dry ice. The powder was immediately added to 20 ml of extraction buffer followed by 0.5 volumes of phenol/chloroform (1:1 v/v), and the mixture was placed on ice. A 0.25 volume of phenol/chloroform (1:1 v/v) was added and the phases were separated by centrifugation at 800×g for 10 minutes. The aqueous phase was removed, placed on ice in a fresh 50 ml tube containing a few drops of phenol/chloroform (1:1 v/v). The organic phase was mixed with 2 ml of extraction buffer, incubated in a water bath at 68° C. for 5 minutes, and centrifuged as above. The aqueous phase was combined with that saved on ice. The aqueous phase was extracted four times with phenol/chloroform (1:1 v/v) until there was no protein at the interface. To precipitate the RNA, 0.1 volume of 3 M sodium acetate pH 5.2 plus 2.5 volumes of 95% ethanol was added and the mixture was frozen at −20° for 2 hours. The RNA was pelleted by centrifugation at 12,000×g for 20 minutes and resuspended in 450 µl of DEP-treated water. A 2 µl aliquot of each total RNA preparation was electrophoresed on a 0.8% agarose gel using TAE buffer to check the quality of the RNA.

Poly-A RNA was isolated using a mRNA Separator kit (Clonetech, Palo Alto, Calif.) according to the manufacturer's protocols.

Example 4

Isolation of Plasmid DNA from the Genomic Library Clones

Each 384 well plate containing genomic clones was used to inoculate 4–96-well deep well plates containing 1.25 ml of Magnificent Broth (MacConnell Research, San Diego, Calif.) supplemented with ampicillin at 50 µg/ml. The 96-well deep plates were incubated at 37° C. for 22–24 hours at 300 rpm. The plates were centrifuged at 800×g for 10 minutes. Plasmid DNA was isolated using a Qiaprep Turbo Core kit (QIAGEN, Chatsworth, Calif.) and the Qiagen BioRobot 9600 (QIAGEN, Chatsworth, Calif.). The 96 well plates containing the plasmid DNA were dried down in a SpeedVac (Savant Instruments, Inc., Holbrook, N.Y.) followed by the addition of 15 µl of 3×SSC to each well using a Hydra HTS workstation (Robbins Scientific, Sunnyvale, Calif.).

Example 5

Printing of DNA Microarrays

Four 96 well plates were rearrayed back to 384 well plates using the Robbins HTS workstation. A 5 µl volume of each plasmid was aliquoted into 384-well microplates. From these plates, the plasmids were spotted onto poly-L-lysine coated glass microscope slides using the equipment and methods that are described on the web site of Professor P. O. Brown of Stanford University (http://cmgm.stanford.edu/pbrown/protocols). The density of spots was 10,000 per slide.

Example 6

Probe Preparation and Hybridization

Fluorescent probes were prepared by reverse transcription of 1 µg of polyA RNA from *Ceriporiopsis subvermispora* to incorporate aminoallyl-dUTP into first strand cDNA. The amino-cDNA products were subsequently labeled by direct coupling to either Cy3 or Cy5 monofunctional reactive dyes (Amersham Pharmacia Biotech, Arlington Heights, Ill.). The details of this protocol are described at http://cmgm.stanford.edu/pbrown/protocols. Cy3 and Cy5 labeled probes were combined and purified using Qiaquick PCR spin columns (Qiagen, Valencia, Calif.). The purified probes were dried under vacuum in a SpeedVac, resuspended in 18 µl of water and combined with the following: 3.6 µl of 20×SSC, 1.8 µl of poly-dA (500 µg/ml; Amersham Pharmacia Biotech), and 0.54 µl of 10% SDS. Before hybridization, the solution was filtered with a 0.22 µm Ultrafree-MC microcentrifuge filter (Millipore, Beford, Mass.), boiled for 2 minutes, and cooled to room temperature. The probe was then applied to the microarray under a coverglass, placed in a humidified chamber, and incubated at 65° C. overnight. Before scanning, the arrays were washed consecutively in 1×SSC with 0.03% SDS, 0.2×SSC, and 0.05×SSC, and centrifuged for 2 minutes at 500 rpm to remove excess liquid. Lastly, the slides were imaged using a custom-built confocal laser microscope (Eisen and Brown, 1999, *Methods in Enzymology* 303: 179).

Example 7

Characterization of Clones Induced by Pulp

From the first 20,000 genomic clones, 20 clones were determined to contain DNA whose expression was induced on hardwood thermomechanical pulp. For each of the clones plasmid DNA was isolated by going back to the well on the 384 plate containing the desired clone and inoculating into a 15 ml falcon tube containing 3 ml of Luria Broth (LB) and 100 µg/ml of ampicillin. The clones were grown overnight at 37° C., 250 rpm. The plasmids were isolated using the Qiagen robot protocol (Qiagen, Chatsworth, Calif.) and sequenced using 150 ng of plasmid template, 1.6 ng of M13 primer (forward or reverse), and water to 6 µl. The samples were run on an ABI 3700 sequencer (Applied Biosystems, Foster City, Calif.). One of the clones, pCsubHP1 contained a genomic fragment, which shared considerable identity to known peroxidases but did not contain the whole gene.

Example 8

Utilizing RLM-RACE to Amplify the Complete Coding Sequences of the Clones.

Total RNA was prepared according to the method outlined in Example 3. All of the steps in the RLM-RACE reaction were carried with materials provided in a GeneRacer Kit (Invitrogen, Carlsbad, Calif.) according to the manufacturer's instructions. The RNA was subjected to dephosphorylation using 14 µl of total RNA (~1 µg), 2 µl CIP buffer, 2

µl RNaseOut (40 U/µl), and 2 µl CIP (10 U/µl). The reaction was mixed by pipette and vortexed briefly after which it was incubated at 50° C. for 1 hour. After incubation the reactions were briefly centrifuged and placed on ice.

The RNA was then precipitated according to the following protocol. A 90 µl volume of diethylpyrocarbonate (DEPC) treated water and 100 µl of phenol:chloroform were added to the samples and vortexed vigorously for 30 seconds. The samples were then centrifuged at maximum speed in a microcentrifuge for 5 minutes at room temperature. The aqueous (top) phase was transferred to a new microcentrifuge tube followed by 2 µl of mussel glycogen (10 mg/ml) and 10 µl of 3 M sodium acetate pH 5.2, mixed well, and frozen on dry ice for 10 minutes. The RNA was subsequently pelleted by centrifugation at maximum speed in a microcentrifuge for 20 minutes at 4° C. The supernatant was removed by pipette being careful not to disturb the pellet. A 500 µl volume of 70% ethanol was then added to the pellet, inverted several times, vortexed briefly, and then centrifuged at maximum velocity for 2 minutes at 4° C. in a microcentrifuge. The ethanol was then removed by pipette. The RNA pellet was air dried for 2 minutes at room temperature and then resuspended in 7 µl of DEPC water.

The mRNA cap structure was then removed by adding 7 µl of the dephosphorylated RNA, 1 µl of 10 ×TAP buffer (Invitrogen, Carlsbad, Calif.), 1 µl of RnaseOut (Invitrogen, Carlsbad, Calif.), and 1 µl of TAP (0.5 U/µl) (Invitrogen, Carlsbad, Calif.) and mixing briefly. The fluid was collected by a short centrifuge pulse and subsequently incubated at 37° C. for 1 hour. After incubation the samples were quickly centrifuged and placed on ice. The RNA was then precipitated according to the method outlined in the previous paragraph.

Once the mRNA cap structure was removed, ligation of the GeneRacer RNA oligo was performed using a reaction containing 7 µl of dephosphorylated, decapped RNA added to 0.25 µg of the following GeneRacer RNA oligo. 5'-CGACUGGAGCACGAGGACACUGACAUGGACU GAAGGAGUAGAAA-3' (SEQ ID NO:3)

The mixture was pipetted several times and then incubated at 65° C. for 5 minutes to remove the RNA secondary structure. After incubation the reaction was chilled on ice for 2 minutes followed by a brief centrifugation. To this mixture, 1 µl of 10×ligase buffer, 1 µl of 10 mM ATP, 1 µl of RNaseOut, and 1 µl of T4 RNA ligase (5 U/µl) (New England Biolabs, Beverly, Mass.) were added and incubated for 1 hour at 37° C. The reaction was then centrifuged briefly and placed on ice. A 90 µl volume of diethylpyrocarbonate treated water and 100 µl of phenol:chloroform were added to the samples and vortexed vigorously for 30 seconds. The aqueous (top) phase was transferred to a new microcentrifuge tube followed by 2 µl of mussel glycogen (10 mg/ml), and 10 µl of 3 M sodium acetate (pH 5.2), mixed well, and frozen on dry ice for 10 minutes. This mixture was stored at −200 for overnight.

The frozen RNA mixture was thawed and subsequently pelleted by centrifugation at maximum speed in a microcentrifuge for 20 minutes at 4° C. The supernatant was removed by pipette being careful not to disturb the pellet. 500 µl of 70% ethanol was then added to the pellet, inverted several times, vortexed briefly, and then centrifuged at maximum velocity for 2 minutes at 4° C. in a microcentrifuge. The ethanol was removed by pipette. The RNA pellet was air dried for 2 minutes at room temperature and then resuspended in 7 µl of DEPC water.

Reverse transcription of the mRNA was performed in 5 different reactions each with a different gene specific reverse primer. The primers were constructed to amplify 5' ends of partial gene fragments, which appear to be induced during growth of *Ceriporiopsis subvermispora* on pulp. The sequence was based upon the consensus sequence of the positive array clones. The different gene specific primers were as follows:

(1) Oligo 993348: 5'-TCGAAAGGTGCCGC ATCAATGGTCCC-3' (SEQ ID NO:4) (for the reverse transcription of the CsubHP1 gene encoding a putative manganese peroxidase);

(2) Oligo 993349: 5'-TTCGTCGCGGGCAA GAGCAAAGTCGG-3' (SEQ ID NO:5) (for the reverse transcription of the CsubHP1 gene encoding a putative manganese peroxidase. Located at a different position than Oligo 993348); (3) Oligo 993350: 5'-ACGGTCMCGGAGAGTGTCGGGMGC-3' (SEQ ID NO:6) (for the reverse transcription of the CsubHP1 gene encoding a putative manganese peroxidase. Located at a different position than Oligo 993348 and Oligo 993349).

A 1 µl volume of the gene specific primer and 1 µl of dNTP mix (10 mM each) were added to the ligated RNA (10 µl). This mixture was incubated at 65° C. to remove any RNA secondary structure and then chilled on ice for 2 minutes. Then 4 µl of 5×first strand buffer (Invitrogen, Carlsbad, Calif.), 2 µl of 0.1 M DTT, 1 µl of RNaseOut, and 1 µl of Superscript II RT (Invitrogen, Carlsbad, Calif.) (200 U/µl) were added to the primer and dNTP's, mixed, centrifuged briefly, and incubated at 42° C. for 50 minutes. After the incubation, the reverse transcription reaction was inactivated by heating to 70° C. for 15 minutes, chilled on ice for 2 minutes, and centrifuged briefly. Then 1 µl of RNase H (2 U) was added to the reaction mixture, incubated at 37° C. for 20 minutes, and centrifuged briefly.

Once the cDNA has been synthesized the sequence of interest was amplified by PCR. Once again 5 reactions were carried out using primers (1)–(3) from above in combination with the GeneRacer 5' primer —5'-CGACTGGAGCACGAGGACACTGA-3' (SEQ ID NO:7). The reaction mixture contained 3 µl of GeneRacer 5' primer (10 µM), 1 µl of reverse gene specific primer (10 µM), 2 µl of RT template from the appropriate reaction, 5 µl of 10×Taq buffer, 1 µl of dNTP mix (10 mM each), 2.5 µl of DMSO, 34 µl of water, and 0.5 µl of Taq DNA polymerase. The PCR instrument was programmed to run a touchdown PCR as follows: 1 cycle at 94° C. for 2 minutes; 5 cycles each at 94° C. for 30 seconds then 72° C. for 2 minutes; 5 cycles each at 94° C. for 30 seconds then 70° C. for 2 minutes; 20 cycles each at 94° C. for 30 seconds then 65° C. for 30 seconds followed by 68° C. for 2 minutes; 1 cycle at 68° C. for 10 minutes; and 4° C. hold.

Then 10 µl of each PCR reaction was mixed with 1.1 µl of loading buffer and run on a 0.8% agarose Tris-Borate-EDTA buffer (TBE; 10.8 g Tris-HCl, 5.5 g boric acid, 0.93 g ethylenediamine tetraacetic acid in 1 liter of water) gel containing ethidium bromide at 90V for 1 hour. The products were observed with UV light on a Nucleotech gel visualization system (Nucleotech, San Mateo, Calif.). Those reactions providing correct size PCR products were subjected to a round of nested PCR in order to increase concentration and purity. Nested PCR was carried out with the GeneRacer 5' nested primer and nested variations of the CsubHP1 clones. For example, Oligo 993348 is a nested primer for the cDNA created from the GeneRacer 5'/Oligo 993349 reaction, as well as the GeneRacer 5'/Oligo 993350 reaction. Also, Oligo 993349 is a nested primer for the GeneRacer 5'/Oligo 993350 reaction. The following reactions were run under the same PCR conditions described above but utilizing different templates and nested primers:

GeneRacer 5'/Oligo 993349 PCR product template with the GeneRacer 5' nested primer and Oligo 993348.

GeneRacer 5'/Oligo 993350 PCR product template with GeneRacer 5' nested primer and primer Oligo 993348.

These PCR products were analyzed by agarose gel and UV analysis as for the first PCR reaction protocol described above. Products, which were relatively pure, were directly ligated into the TOPO-TA vector (Invitrogen, Carlsbad, Calif.) according to the manufacturer's instructions. A 4 μl volume of fresh PCR product, 1 μl of 1.2M NaCl, 0.06 M MgCl$_2$ solution, and 1 μl of the TOPO-TA vector were mixed with a pipette and incubated at room temperature for 30 minutes.

After the incubation, 2 μl of the mixture was used to transform OneShot competent *E. coli* cells (Invitrogen, Carlsbad, Calif.). A 2 μl volume of the ligation mixture was added to the *E. coli* cells and incubated on ice for 5 minutes. Subsequently the cells were heat shocked for 30 seconds at 42° C., and then placed on ice for 2 minutes. A 250 μl volume of SOC media (20 g Bacto Tryptone, 5 g of yeast extract, 2 ml of 5M NaCl, 2.5 ml of 1 M KCl, water to 1 liter) was added to these cells and the mixture was incubated for 1 hour at 37° C. and 250 rpm. After the incubation the colonies were spread on 2×YT plates (15 g of Bacto Tryptone, 10 g of yeast extract, 5 g of NaCl, water to 1 liter) supplemented with 100 μg/ml of ampicillin and incubated at 37° C. overnight for selection of the plasmid. Colonies, which grew on the plates, were picked with a sterile toothpick and grown overnight at 37° C., 250 rpm in a 15 ml Falcon tube containing 3 ml of Luria Broth (LB) and 100 μg/ml of ampicillin. The plasmids were isolated using the Qiagen robot protocol (Qiagen, Chatsworth, Calif.). A 2 μl volume of the resulting plasmid minipreps were digested with 0.5 μl of EcoRI, 2 μl of H buffer (Promega, Madison, Wis.), and 15.5 μl of water for 2 hours at 37° C. The digestion reactions were analyzed by agarose gel chromatography and UV analysis as previously described for the PCR reactions.

Isolated plasmids containing an insert of correct size were sequenced using 150 ng of plasmid template, 1.6 ng of M13 primer (forward or reverse), and water to 6 μl. These samples were run on an ABI 3700 Sequencer (Applied Biosystems, Foster City, Calif.) according to the manufacturer's instructions. Sequence analysis was carried out using Sequencer tools (Genecodes, Ann Arbor, Mich.) and blast alignments allowing for the identification of the entire open reading frame for the desired gene.

Example 9

Constructing Full Length Clones of Desired Genes

With the partial sequence, the full-length manganese peroxidase gene (MnP) was cloned. The cloning was based upon a unique ClaI (or EcoRI) site which would allow for a cDNA/genomic DNA hybrid replica of the full length manganese peroxidase gene. The 5' end of the sequence was amplified by PCR using the 5' MnP-TOPO clone as a template and the following two primers:

Oligo 993449: 5'-CCCCATGGCTTTCGCCTCTCTCTT-3' (SEQ ID NO:8)

The bold face shows the incorporated NcoI site and Oligo 993348 as the reverse primer The 5' end of the MnP was amplified by PCR using the CsubHP1 clone from the library construct as a template and the following two primers:

Oligo 991854: 5'- GAATTCTTGGCTGGTCGCCCTAA-3' (SEQ ID NO:9)

The bold face shows an EcoRI site

Oligo 993450: 5'- AAGTTAATTAACTAAGCAGG GCCAGTAAA-3' (SEQ ID NO:10)

The bold face shows an incorporated PacI site

The PCR reaction was conducted under the same conditions as outlined for the PCR of the RACE products. The resulting products of these two reactions were cloned into the TOPO-TA vectors and sequenced as above. The two PCR products have unique overlapping ClaI and EcoRI sites which allowed them to be joined by a triple ligation with the desired vector. An NcoI/ClaI fragment of the 5' MnP-TOPO clone and a ClaI/PacI fragment of the 3' MnP-TOPO clone can be ligated into the NcoI/PacI digested pAILo1 expression vector. Furthermore, a SpeI/ClaI digested fragment of the 5' MnP-TOPO vector can be ligated into the SpeI/ClaI digested 3' MnP-TOPO vector resulting in the complete hybrid MnP clone in the TOPO vector for deposit.

The digested fragments were run on an agarose gel as above, extracted by razor blade excision, and purified using a Qiaquick spin column (Qiagen, Chatsworth, Calif.). The ligations were conducted overnight using 6.5 μl of gel purified insert DNA, 2 μl of gel purified vector DNA, 1 μl of T4 buffer, and 0.5 μl of T4 DNA ligase. The ligations were transformed into OneShot competent *E. coli* (Invitrogen, Carlsbad, Calif.), miniprepped, and digested as previously outlined. The complete MnP-TOPO clones that gave desired digestion patterns were sequenced. One clone designated *E. coli* TOP10 pCsubHP1F was deposited on Mar. 7, 2002 as NRRL B-30561 with the Agricultural Research Service Patent Culture Collection, Northern Regional Research Center, 1815 University Street, Peoria, Ill., 61604.

Example 10

Nucleotide Sequencing and Characterization of the Full-Length *Ceriporiopsis subvermispora* Peroxidase Clone DNA sequencing of the full-length clone, designated *E. coli* TOP10 pCsubHP1 F, was performed with an Applied Biosystems Model 3700 Automated DNA Sequencer using dye-terminator chemistry.

The peroxidase clone encoded an open reading frame of 1249 bp encoding a polypeptide of 378 amino acids. The nucleotide sequence (SEQ ID NO:1) and deduced amino acid sequence (SEQ ID NO:2) are shown in FIG. 1. Using the SignalP program (Nielsen et al., 1997, *Protein Engineering* 10: 1–6), a signal peptide of 18 residues was predicted. Thus, the mature peroxidase is composed of 360 amino acids. The open reading frame is interrupted by two predicted introns.

A comparative alignment of peroxidase sequences was undertaken using the Clustal method (Higgins, 1989, CABIOS 5: 151–153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

The comparative alignment showed that the *Ceriporiopsis subvermispora* peroxidase shares 81% identity with the manganese peroxidase 2 from *Phanerochaete chrysosporium* (EMBL Accession number L29039). There are 4 potential N-linked glycosylation sites (Asn-X-Ser/Thr) within the *Ceriporiopsis subvermispora* peroxidase. Three of the potential glycosylation sites are conserved in the *Phanerochaete chrysosporium* manganese peroxidase 2. The comparative alignment also showed that the *Ceriporiopsis subvermispora* peroxidase shares 80% identity with the manganese peroxidase 1, 3 and 4 from *Phanerochaete chrysosporium* (EMBL Accession Numbers M60672, U70998, and J04980).

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| *E. coli* TOP10 pCsubHP1F | NRRL B-30561 | Mar. 7, 2002 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

---

What is claimed is:

1. A method for isolating a gene encoding an enzyme, comprising:
    (a) adding a mixture of labeled first nucleic acid probes, isolated from a microbial strain cultured on medium without an inducing substrate, and labeled second nucleic acid probes, isolated from the microbial strain cultured on medium with the inducing substrate, to an array of random genomic DNA fragments of unknown sequence and unknown function of the microbial strain under conditions where the labeled nucleic acids hybridize to complementary sequences of the random genomic DNA fragments in the array, wherein the first nucleic acid probes are labeled with a first reporter and the second nucleic acid probes are labeled with a second reporter, wherein the inducing substrate is selected from the group consisting of cellulose, hemicellulose, lignin, phytic acid, starch, pectin, and protein;
    (b) examining the array under conditions wherein the relative expression of the genes of the microbial strain is determined by the observed hybridization reporter signal of each spot in the array in which (i) the random genomic DNA fragments in the array that hybridize to the first nucleic acid probes produce a distinct first hybridization reporter signal or to the second nucleic acid probes produce a distinct second hybridization reporter signal indicating induction of a gene by the presence of the inducing substrate in the culture medium of the microorganism, and (ii) the random genomic DNA fragments in the array that hybridize to both the first and second nucleic acid probes produce a distinct combined hybridization reporter signal; and
    (c) isolating from the microbial strain the gene induced by the presence of the substrate, wherein the gene encodes an enzyme that degrades the substrate.

2. The method of claim 1, wherein the enzyme is an oxidoreductase, transferase, hydrolase, lyase, isomerase, or ligase.

3. The method of claim 1, wherein the microbial strain is a bacterium or fungus.

4. The method of claim 3, wherein the fungus is a yeast or a filamentous fungus.

5. The method of claim 3, wherein the bacterium is a *Bacillus, Pseudomonas,* or *Streptomyces* strain.

6. The method of claim 4, wherein the yeast is a *Candida, Kluyveromyces, Pichia, Saccharomyces, Schizosaccharomyces,* or *Yarrowia* strain.

7. The method of claim 4, wherein the filamentous fungus is selected from the group consisting of an *Acremonium, Aspergillus, Aureobasidium, Bjerkandera, Ceriporiopsis, Coprinus, Coriolus, Cyptococcus, Filibasidium, Fusarium, Humicola, Magnaporthe, Mucor, Myceliophthora, Neocallimastix, Neurospora, Pecilomyces, Penicillium, Phanerochaete, Phlebia, Piromyces, Pleurotus, Schizophyllum, Talaromyces, Thermoascus, Thielavia, Tolypocladium, Trametes,* and *Trichoderma* strain.

8. The method of claim 1, wherein the random genomic DNA fragments are at least about 50 bp in length.

9. The method of claim 1, wherein the hybridization conditions are selected from the group consisting of very low, low, low-medium, medium, medium-high, high, and very high stringency conditions.

10. A method for isolating a gene encoding an enzyme, comprising:
    (a) adding a mixture of labeled first nucleic acid probes, isolated from a first microbial strain cultured on medium without an inducing substrate, and labeled second nucleic acid probes, isolated from the first microbial strain cultured on medium with the inducing substrate, to an array of random nucleic acid fragments of unknown sequence and unknown function of a second microbial strain under conditions where the labeled nucleic acids hybridize to complementary sequences of the random nucleic acid fragments in the array, wherein the first nucleic acid probes are labeled with a first reporter and the second nucleic acid probes are labeled with a second reporter;
    (b) examining the array under conditions wherein the relative expression of the genes of the microbial strain is determined by the observed hybridization reporter signal of each spot in the array in which (i) the random nucleic acid fragments in the array that hybridize to the first nucleic acid probes produce a distinct first hybridization reporter signal or to the second nucleic acid probes produce a distinct second hybridization reporter signal indicating induction of a gene by the presence of the inducing substrate in the culture medium of the microorganism, and (ii) the random nucleic acid fragments in the array that hybridize to both the first and second nucleic acid probes produce a distinct combined hybridization reporter signal; and
    (c) isolating from the first microbial strain a gene induced by the presence of the substrate, wherein the gene encodes an enzyme that degrades the substrate.

11. The method of claim 10, wherein the inducing substrate is selected from the group consisting of cellulose, hemicellulose, lignin, phytic acid, starch, pectin, and protein.

12. The method of claim 10, wherein the enzyme is an oxidoreductase, transferase, hydrolase, lyase, isomerase, or ligase.

13. The method of claim 10, wherein the enzyme is a peroxidase.

14. The method of claim 10, wherein the microbial strain is a bacterium or fungus.

15. The method of claim 14, wherein the fungus is a yeast or a filamentous fungus.

16. The method of claim 14, wherein the bacterium is a *Bacillus, Pseudomonas,* or *Streptomyces* strain.

17. The method of claim 15, wherein the yeast is a Candida, *Kluyveromyces, Pichia, Saccharomyces, Schizosaccharomyces,* or *Yarrowia* strain.

18. The method of claim 15, wherein the filamentous fungus is selected from the group consisting of an *Acremonium, Aspergillus, Aureobasidium, Bjerkandera, Ceriporiopsis, Coprinus, Coriolus, Cryptococcus, Filibasidium, Fusarium, Humicola, Magnaporthe, Mucor, Myceliophthora, Neocallimastix, Neurospora, Pecilomyces, Penicillium, Phanerochaete, Piromyces, Pleurotus, Schizophyllum, Talaromyces, Thermoascus, Thielavia, Tolypocladium, Trametes,* and *Trichoderma* strain.

19. The method of claim 10, wherein the random nucleic acid fragment is a random genomic fragment.

20. The method of claim 10, wherein the random nucleic acid fragment is a random cDNA fragment.

21. The method of claim 10, wherein the random nucleic acid fragments are at least about 50 bp in length.

22. The method of claim 10, wherein the hybridization conditions are selected from the group consisting of very low, low, low-medium, medium, medium-high, high, and very high stringency conditions.

23. An isolated polypeptide having peroxidase activity, comprising an amino acid sequence which has at least 95% identity with amino acids 19 to 316 of SEQ ID NO: 2, wherein all amino acid substitutions are conservative; or a fragment thereof, which has peroxidase activity.

24. The polypeptide of claim 23, having an amino acid sequence which has at least 95% identity with amino acids 19 to 316 of SEQ ID NO: 2, wherein all amino acid substitutions are conservative.

25. The polypeptide of claim 23, comprising the amino acid sequence of SEQ ID NO: 2.

26. The polypeptide of claim 23, consisting of the amino acid sequence of SEQ ID NO: 2 or a fragment thereof, which has peroxidase activity.

27. The polypeptide of claim 26, consisting of the amino acid sequence of SEQ ID NO: 2.

28. The polypeptide of claim 26, which consists of amino acids 19 to 316 of SEQ ID NO: 2.

29. The polypeptide of claim 23, which is encoded by the nucleic acid sequence contained in plasmid pCsubHP1F which is contained in *E. coli* NRRL B-30561.

30. A method for producing the polypeptide of claim 23, comprising (a) cultivating a strain under suitable conditions for the production of the polypeptide, wherein the strain in its wild-type form is capable of producing the polypeptide; and (b) recovering the polypeptide from the cultivation medium.

31. An isolated nucleic acid sequence encoding a polypeptide having peroxidase activity, wherein the nucleic acid sequence encodes a polypeptide comprising an amino acid sequence which has at least 95% identity with amino acids 19 to 316 of SEQ ID NO: 2, wherein all amino acid substitutions are conservative; or a subsequence thereof, wherein the subsequence encodes a polypeptide fragment which has peroxidase activity.

32. The nucleic acid sequence of claim 31, encoding a polypeptide comprising an amino acid sequence which has at least 95% identity with amino acids 19 to 316 of SEQ ID NO: 2, wherein all amino acid substitutions are conservative.

33. The nucleic acid sequence of claim 31, encoding a polypeptide comprising the amino acid sequence of SEQ ID NO: 2.

34. The nucleic acid sequence of claim 31, encoding a polypeptide consisting of the amino acid sequence of SEQ ID NO: 2 or a fragment thereof having peroxidase activity.

35. The nucleic acid sequence of claim 34, encoding a polypeptide consisting of the amino acid sequence of SEQ ID NO: 2.

36. The nucleic acid sequence of claim 34, encoding a polypeptide consisting of amino acids 19 to 316 of SEQ ID NO: 2.

37. The nucleic acid sequence of claim 31, encoding a polypeptide wherein all amino acid substitutions are conservative substitutions of amino acids 19 to 316 of SEQ ID NO: 2.

38. A nucleic acid construct comprising the nucleic acid sequence of claim 31 operably linked to one or more control sequences that direct the production of the polypeptide in a suitable expression host.

39. A recombinant expression vector comprising the nucleic acid construct of claim 38.

40. A recombinant host cell comprising the nucleic acid construct of claim 38.

41. A method for producing a polypeptide having peroxidase activity, comprising (a) cultivating the recombinant host cell of claim 40 under conditions suitable for production of the polypeptide; and (b) recovering the polypeptide.

42. An isolated nucleic acid sequence comprising a nucleic acid sequence having at least one mutation in the mature polypeptide coding sequence of SEQ ID NO: 1, in which the mutant nucleic acid sequence encodes a polypeptide comprising amino acids 19 to 316 of SEQ ID NO: 2.

43. A nucleic acid construct comprising a gene encoding a protein, wherein the gene is operably linked to a nucleic acid sequence consisting of nucleotides 1 to 54 of SEQ ID NO: 1 which encode a signal peptide, wherein the gene is foreign to the nucleic acid sequence.

44. A recombinant expression vector comprising the nucleic acid construct of claim 43.

45. A recombinant host cell comprising the nucleic acid construct of claim 43.

46. A method for producing a protein comprising (a) cultivating the recombinant host cell of claim 45 under conditions suitable for production of the protein; and (b) recovering the protein.

47. A method for isolating a gene encoding a peroxidase, comprising:

(a) adding a mixture of labeled first nucleic acid probes, isolated from a microbial strain cultured on medium without an inducing substrate, and labeled second nucleic acid probes, isolated from the microbial strain cultured on medium with the inducing substrate to an array of random nucleic acid fragments of the microbial strain under conditions where the labeled nucleic acids hybridize to complementary sequences of the random nucleic acid fragments in the array, wherein the first nucleic acid probes are labeled with a first reporter and the second nucleic acid probes are labeled with a second reporter;

(b) examining the array under conditions wherein the relative expression of the genes of the microbial strain is determined by the observed hybridization reporter signal of each spot in the array in which (i) the random nucleic acid fragments in the array that hybridize to the first nucleic acid probes produce a distinct first hybridization reporter signal or to the second nucleic acid probes produce a distinct second hybridization reporter signal indicating induction of a gene by the presence of the inducing substrate in the culture medium of the microorganism, and (ii) the random nucleic acid fragments in the array that hybridize to both the first and second nucleic acid probes produce a distinct combined hybridization reporter signal; and (c) isolating from the microbial strain the gene induced by the presence of the substrate and encodes a peroxidase that degrades the substrate.

48. The method of claim 47, wherein the inducing substrate is selected from the group consisting of cellulose, hemicellulose, lignin, phytic acid, starch, pectin, and protein.

49. The method of claim 47, wherein the microbial strain is a bacterium or fungus.

50. The method of claim 49, wherein the fungus is a yeast or a filamentous fungus.

51. The method of claim 49, wherein the bacterium is a *Bacillus, Pseudomonas,* or *Streptomyces* strain.

52. The method of claim 50, wherein the yeast is a *Candida, Kluyveromyces, Pichia, Saccharomyces, Schizosaccharomyces,* or *Yarrowia* strain.

53. The method of claim 50, wherein the filamentous fungus is selected from the group consisting of an *Acremonium, Aspergillus, Aureobasidium, Bjerkandera, Ceriporiopsis, Coprinus, Coriolus, Cryptococcus, Filibasidium, Fusarium, Humicola, Magnaporthe, Mucor, Myceliophthora, Neocllimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* and *Trichoderma* strain.

54. The method of claim 47, wherein the random nucleic acid fragment is a random genomic fragment.

55. The method of claim 47, wherein the random nucleic acid fragment is a random cDNA fragment.

56. The method of claim 47, wherein the random nucleic acid fragments are at least about 50 bp in length.

57. The method of claim 47, wherein the hybridization conditions are selected from the group consisting of very low, low, low-medium, medium, medium-high, high, and very high stringency conditions.

* * * * *